US007342221B2

(12) United States Patent
Takenaka et al.

(10) Patent No.: US 7,342,221 B2
(45) Date of Patent: Mar. 11, 2008

(54) RADIATION IMAGE PICK-UP DEVICE, RADIATION IMAGE PICK-UP METHOD, AND IMAGE PICK-UP SYSTEM

(75) Inventors: Katsuro Takenaka, Saitama (JP); Tadao Endo, Saitama (JP); Toshio Kameshima, Saitama (JP); Tomoyuki Yagi, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 415 days.

(21) Appl. No.: 10/991,436

(22) Filed: Nov. 19, 2004

(65) Prior Publication Data

US 2005/0109927 A1    May 26, 2005

(30) Foreign Application Priority Data

Nov. 20, 2003   (JP)   ............................. 2003-391063
Jun. 11, 2004   (JP)   ............................. 2004-174520

(51) Int. Cl.
*G12B 13/00*   (2006.01)

(52) U.S. Cl. .................................................. 250/252.1
(58) Field of Classification Search ............. 250/252.1, 250/370.09, 370.11; 378/98.7, 98.8, 98.9, 378/207
See application file for complete search history.

(56) References Cited

U.S. PATENT DOCUMENTS

| | | | | |
|---|---|---|---|---|
| 5,381,458 A * | 1/1995 | Deslattes | .................... | 378/207 |
| 6,075,256 A | 6/2000 | Kaifu et al. | .................... | 257/53 |
| 6,219,405 B1 * | 4/2001 | Inoue | .................... | 378/98.8 |
| 6,271,880 B1 | 8/2001 | Kameshima et al. | .................... | 348/244 |
| 6,333,963 B1 * | 12/2001 | Kaifu et al. | .................... | 378/98.2 |
| 6,512,279 B2 | 1/2003 | Kaifu et al. | .................... | 257/448 |
| 6,568,851 B2 * | 5/2003 | Saito | .................... | 378/207 |
| 6,600,805 B2 * | 7/2003 | Hansen | .................... | 378/53 |
| 6,632,020 B2 * | 10/2003 | Kaufhold et al. | .................... | 378/207 |
| 6,818,899 B2 | 11/2004 | Endo | .................... | 250/370.14 |
| 2001/0050402 A1 | 12/2001 | Kaifu et al. | .................... | 257/431 |
| 2002/0167061 A1 | 11/2002 | Kaifu et al. | .................... | 257/431 |
| 2004/0159901 A1 | 8/2004 | Kaifu et al. | .................... | 257/431 |
| 2006/0071174 A1 * | 4/2006 | Spartiotis et al. | ....... | 250/370.13 |
| 2006/0180766 A1 * | 8/2006 | Difilippo | ................ | 250/363.09 |
| 2006/0280281 A1 * | 12/2006 | Flohr et al. | .................... | 378/5 |
| 2007/0131862 A1 * | 6/2007 | Cowan et al. | .......... | 250/339.09 |

FOREIGN PATENT DOCUMENTS

JP   08-116044 A   5/1996

* cited by examiner

*Primary Examiner*—David Porta
*Assistant Examiner*—David S Baker
(74) *Attorney, Agent, or Firm*—Fitzpatrick, Cella, Harper & Scinto

(57) ABSTRACT

A plurality of correction images are obtained while changing the radiation energy of an incident radiation in the absence of an object. Subsequently, an object image is obtained in the presence of the object by emitting the radiation to the object. Then, the object image is corrected by using a correction image obtained under a radiation energy condition closest to the radiation energy of the obtained object image.

27 Claims, 14 Drawing Sheets

[PRIOR]

| | THICKNESS (μm) | ※ WHITE IMAGE 60kV | ※ RADIOGRAPHING OBJECT IMAGE 85kV | X-ray ABSORPTIVITY (85kV/60kV) | NORMAL=1 |
|---|---|---|---|---|---|
| NORMAL | 500 | 0.85 | 0.48 | 0.56 | |
| SPLASH CONCAVE | 400 | 0.78 | 0.40 | 0.52 | 0.92 |
| SPLASH CONVEX | 600 | 0.90 | 0.54 | 0.60 | 1.07 |

[1st EMBODIMENT]

| | THICKNESS (μm) | ※ WHITE IMAGE 90kV | ※ RADIOGRAPHING OBJECT IMAGE 85kV | X-ray ABSORPTIVITY (85kV/90kV) | NORMAL=1 |
|---|---|---|---|---|---|
| NORMAL | 500 | 0.42 | 0.48 | 1.14 | |
| SPLASH CONCAVE | 400 | 0.35 | 0.40 | 1.15 | 1.01 |
| SPLASH CONVEX | 600 | 0.48 | 0.54 | 1.13 | 0.99 |

※ -MARKED VALUES DENOTE X-ray ABSORPTIVITY IN RELATION TO RESPECTIVE THICKNESSES IN GRAPH

FIG. 3

PHOTO DETECTOR ARRAY SIDE

CsI X-ray ABSORPTIVITY

RADIATION IMAGE PICK-UP DEVICE, RADIATION IMAGE PICK-UP METHOD, AND IMAGE PICK-UP SYSTEM

BACKGROUND OF THE INVENTION

1. Field of the Invention

The present invention relates to a radiation image pick-up device, a radiation image pick-up method and a radiation image pick-up system which correct a radiographed object image.

2. Related Background Art

Currently, X-ray image pick-up devices used for medical diagnosis mainly use a so-called film system in which an X-ray is emitted to a human body, the X-ray having passed through the human body is applied to a scintillator for converting the X-ray into a visible radiation, and a fluorescence is exposed to a film.

However, more efficient diagnosis and more accurate medical devices are strongly demanded in hospitals of the world as well as in Japan which is becoming an aging society. Under such circumstances, because of a film development process of X-ray image pick-up devices using the conventional film system, it takes a long time before a doctor obtains an X-ray image of a patient. When a patient moves during X-ray radiographing or exposure is not correct, radiographing has to be performed again. These factors interfere with higher efficiency of diagnosis in hospitals and put a heavy burden on patients, resulting in a serious difficulty in establishing a new medical society for the future.

In recent years, the "digitalization of X-ray image information" has grown in demand among health care providers. If digitalization is achieved, doctors can obtain X-ray image information on patients with optimum angles in real time and the obtained X-ray image information can be recorded and managed using media such as a magneto-optical disc. By using networks and other communication systems, X-ray image information on patients can be transmitted to any hospital of the world in a short time. In order to meet the needs for the "digitalization of X-ray image information", X-ray image pick-up devices using CCD solid state imaging devices and amorphous silicon photoelectric conversion elements instead of a film have been proposed in recent years.

FIG. 8 is a schematic sectional view showing a digital X-ray image pick-up device, which has been developed in recent years. The following will briefly describe the configuration of the device (e.g., Japanese Patent Application Laid-Open No. H08-116044).

Photoelectric conversion elements 21 using amorphous silicon and switching TFTs 22 are formed on a glass substrate 20. A protective layer 27 made of silicon nitride or the like covers the entire substrate to protect the elements. A reading circuit 28 for drawing electrical signals from the photoelectric conversion elements 21 to the outside (outside the substrate) and a shift register (not shown) for driving the TFTs are connected to the outer periphery of the glass substrate. The overall configuration serves as a photodetector array 8. A fluorescent screen 142 for converting a wavelength from an X-ray to a visible radiation is formed on the upper part of the photodetector array 8 by using a method such as bonding, so that the digital X-ray image pick-up device is finished.

As shown in FIG. 8, in the case of the digital X-ray image pick-up device, an X-ray 29 is incident from a point above the fluorescent screen 142, the X-ray 29 is subjected to wavelength conversion into a visible radiation 30 through the fluorescent screen 142, and the converted visible radiation 30 is detected by the photoelectric conversion element 21. Further, the detected light is converted into an analog electrical signal 80 and the signal is sequentially drawn to the reading circuit 28 by turning on/off the TFTs 22. Thereafter, the signal is converted into a digital signal 42 by an AD converter 40 which is provided in the subsequent stage of the reading circuit 28. The converted digital signal 42 is transferred to the image processing unit 10 and is subjected to image processing such as offset correction and gain correction, and the signal is displayed on a display 160, and then a diagnosis is performed by a doctor 106.

The following will describe actual radiographing using the digital X-ray image pick-up device.

FIG. 9 is a flowchart from the installation of the digital X-ray image pick-up device in a hospital to actual radiographing performed on a patient.

The digital X-ray image pick-up device having been carried out from a factory is subjected to several adjustments after being installed in a hospital. Calibration is always performed before actual radiographing. Calibration means radiographing performed by applying an X-ray with no radiographed object between an X-ray generator and the digital X-ray image pick-up device. Calibration data (hereinafter, referred to as a white image) serves as gain correction data when an object is actually radiographed. Thus, a radiographed white image is stored in a memory device 53 or the like and is read for gain correction every time radiographing is performed.

In the case of the digital X-ray image pick-up device using photoelectric conversion elements of amorphous silicon or the like, it is necessary to consider the correction of variations in sensitivity for each of the photoelectric conversion elements, variations in gain in the reading circuit, and the shading of the fluorescent screen and an X-ray. Thus, it is necessary to divide an object radiograph image by a white image. This processing is called white correction. Conventionally, a white image is radiographed under a certain condition (X-ray tube voltage/X-ray tube current/X-ray exposure time/X-ray tube vessel—a distance between digital X-ray image pick-up devices) and the image is used over a week, a month and a year. During this period, normal radiographing 52 of FIG. 9 is repeated.

After calibration, object (patient) information and radiographed portion information are inputted, radiographing conditions are determined, and radiographing is actually performed. At this point, the radiographing conditions are varied according to a radiographed portion and a thickness of an object. For example, a tube voltage (X-ray energy) and so on are adjusted in kilovolts. For this reason, the radiographing conditions of a white image and the radiographing conditions of an object do not match with one another. After radiographing, correction is performed in which a white image is read from the memory device 53, and white correction is performed on an object image in an image processing unit, and then the image is shown on a display.

The X-ray generator will be briefly described below because the present invention closely relates to X-ray absorption.

FIG. 10 is a schematic sectional view showing an X-ray tube which serves as an X-ray source in the X-ray generator.

Vacuum is almost maintained in the X-ray tube. By applying a voltage (several tens kV) between an anode and a cathode, electrons are accelerated from the cathode to the anode and collide with a target, so that an X-ray is generated. When an X-ray is generated by the X-ray generator, a tube voltage and a tube current are mainly adjusted. The tube voltage indicates a voltage applied to the cathode and the anode. As the tube voltage increases, the acceleration of electrons increases, thereby increasing the "energy" of the electrons. Further, the tube current indicates a current applied to a filament. As the tube current increases, the "number" of electrons outputted from the filament increases, thereby increasing the intensity of an X-ray. Therefore, although the intensity (number/amount) of an X-ray is increased by changing the tube current, "energy" does not increase.

An X-ray has various interactions (Rayleigh scattering, a photoelectric effect and so on) when passing through a substance. The way to interact varies according to the "energy" of an X-ray. Hence, the energy of a generated X-ray is varied by changing the tube voltage of the X-ray generator. Further, the interaction (amount of absorption/amount of transmission) with a substance is also changed.

The following will describe a scintillator used in the digital X-ray image pick-up device.

Currently, a main scintillator is $Gd_2O_2S:Tb^{3+}$, CsI:Tl and so on. $Gd_2O_2S:Tb^{3+}$ is prepared by coating/drying a scintillator and a binder resin on a PET (polyethylene terephthalate) sheet or the like. Although $Gd_2O_2S:Tb^{3+}$ can be mass-manufactured and is inexpensive, a large amount of light is scattered because $Gd_2O_2S:Tb^{3+}$ is a particulate scintillator, resulting in a low resolution. In contrast, CsI:Tl is a scintillator of a columnar structure and thus causes less scattered light with a higher resolution as compared with $Gd_2O_2S:Tb^{3+}$. Further, a high brightness can be obtained by a large thickness. For this reason, CsI:Tl is widely used at present as a scintillator of the digital X-ray image pick-up device. Regarding CsI, Tl and Na are mainly used as activators at present. The activator is not particularly limited and thus will be referred to as CsI.

The following will describe the configuration and manufacturing method of CsI.

FIG. 11 is a schematic sectional view showing a CsI fluorescent screen. An X-ray emitted from a substrate 81 passes through the substrate 81 and is absorbed by a scintillator 82, and then wavelength conversion is performed from an X-ray to a visible radiation. Then, the visible radiation having undergone wavelength conversion passes through a protective layer 83 and is detected by a photodetector array which adheres to the protective layer 83. Thus, each material has to be characterized as follows:

[1] Substrate 81: small X-ray absorption

[2] Scintillator 82: large X-ray absorption with a high brightness and a high resolution

[3] Protective layer 83: a high transmittance of a visible radiation

X-ray absorption (transmittance) is determined by the attenuation coefficient and thickness of a material. The smaller atomic number of a material, the smaller attenuation coefficient, resulting in difficulty in absorbing an X-ray (higher transmittance). Moreover, X-ray absorption varies according to a tube voltage (X-ray energy). In general, as energy decreases, absorption increases.

FIG. 12 is a characteristic diagram showing a tube voltage and an X-ray transmittance of glass (85), aluminum (86) and amorphous carbon (87) which are mainly used as base materials. The amorphous carbon 87 has a small atomic number (z=6) and has a small amount of X-ray absorption particularly at a low energy. Thus, the amorphous carbon 87 has a high sensitivity at a low energy as compared with other base material.

A scintillator absorbs an X-ray and emits a visible radiation according to an amount of X-ray absorption. Like the base materials, the X-ray absorption of the scintillator is determined by a material and a thickness. Currently, CsI with a thickness of 500 μm is used most frequently. FIG. 13 is a characteristic diagram showing an X-ray absorptivity in CsI having a thickness of 100 to 500 μm.

The tube voltage characteristic of an X-ray in the scintillator and the base materials is determined by the kind of material and a thickness thereof and thus the tube voltage is changed by an impurity and a foreign matter or variations in thickness. Particularly in the event of a foreign matter and a partially uneven thickness, a tube voltage characteristic is changed only on that portion.

Generally CsI is formed on a base material by vacuum deposition shown in FIG. 14. The substrate 81 is fit into a substrate holder 88 which is mounted in the upper part of a chamber, CsI powder is put in a port 89 which is mounted in the lower part, and the port 89 is heated, so that CsI is evaporated to form the substrate 81 (resistance heating). Since CsI is a columnar crystal, a column vertically stretches from the substrate 81 under normal conditions. During deposition, CsI powder-dissolves and bumping occurs, resulting in a number of asperities called a splash 90 on a surface of CsI.

The digital X-ray image pick-up device has a large fluorescent screen formed on a large (e.g., 45×45 cm) photodetector array. Hence, it is difficult to prevent the entry of a foreign matter in a process of manufacturing a photodetector array and a fluorescent screen. As a matter of course, the substrate is cleaned particularly in the vapor deposition of CsI. However, the adhesion of only a small foreign matter causes abnormal growth of CsI with the foreign matter acting as a nucleus. FIGS. 15A to 15D are diagrams showing a state of abnormal growth of CsI used as a scintillator (wavelength converter).

FIG. 15A is a schematic diagram showing a state of abnormal growth of CsI used as a scintillator. Since CsI 82 of FIG. 15A is a columnar crystal under normal conditions, the CsI 82 vertically grows from an evaporation surface. When the evaporation surface has a foreign matter 91, the CsI 82 grows diagonally with the foreign matter 91 acting as a nucleus and is changed into asperities several times larger than the nucleus. The asperities (abnormal growth portion) change the thickness of the CsI 82 from a normal portion, so that X-ray absorption is also changed. Further, a tube voltage characteristic is also changed according to a thickness of CsI and thus a ratio of light emission differs between the normal portion and the abnormal growth portion.

FIGS. 15B to 15D are characteristic diagrams showing an amount of light emission in the normal portion and the abnormal growth portion. FIG. 15B shows that the abnormal growth portion and the normal portion are radiographed at a tube voltage of 80 kV. FIG. 15C shows that the abnormal growth portion and the normal portion are radiographed at a tube voltage of 60 kV. FIG. 15D shows a ratio determined by dividing the characteristic of FIG. 15C and the characteristic of FIG. 15B. This division means white correction. In the white correction, division is actually performed using images of different radiographing tube voltages.

As shown in FIG. 15B, the normal portion has an output of 100 in the radiographing at 80 kV, whereas the abnormal growth portion has a smaller output of 80. As shown in FIG. 15C, the normal portion has an output of 100 in the radiographing at 60 kV, whereas the abnormal growth portion has a smaller output of 90. In this way, a change in tube voltage changes a reduction in the output of the abnormal growth portion. This is because the thickness of CsI differs between the abnormal growth portion and the normal portion and thus X-ray absorption is changed.

In the case of the abnormal growth caused by the foreign matter of FIG. 15A, the X-ray absorption of the foreign matter also makes a major contribution. An amount of X-ray reaching CsI decreases according to an amount of X-ray absorbed by the foreign matter, an amount of light emission of CsI decreases, and another tube voltage characteristic is obtained. Due to these causes, a change in the tube voltage of the abnormal growth portion appears as a white correction error during white correction. FIG. 15D shows this state. In FIG. 15D, the normal portion has 100/100=1, whereas the abnormal growth portion has 90/80=1.12, which is a white correction error of 12%.

Further, CsI always has a splash portion in vacuum deposition. Current technology has not found any means for eliminating the splash. The splash is a defect caused by the bumping of CsI and has no fixed amount or size. The splash portion has irregular thicknesses and densities. Hence, the splash portion is different from other normal portions in X-ray absorption. Thus, like abnormal growth caused by a foreign matter, white correction causes a white correction error according to a change in the tube voltage characteristic.

Also when a foreign matter enters the substrate 81, a white correction error occurs in the above-described manner. In the above explanation, CsI was discussed as the scintillator 82 of the conventional art. Other scintillators similarly have white correction errors caused by foreign matters.

Moreover, a direct radiation image pick-up device using no scintillator has a similar white correction error. The material of the direct radiation image pick-up device is selected from the group consisting of amorphous selenium, gallium arsenide, mercurous iodide and lead iodide or the like. Like scintillators, a thickness distribution due to the adhesion of a foreign matter occurs during film formation. The generated thickness distribution changes an amount of X-ray absorption like the splash of CsI, causing a white correction error.

SUMMARY OF THE INVENTION

The present invention is devised to solve the problem and has as its object the provision of a radiation image pick-up device, a radiation image pick-up method, and a radiation image pick-up system which reduce correction errors caused by a difference in the amount of X-ray absorption and achieve accurate correction when correcting a radiographed object image, the difference being made by a splash, a foreign matter and so on.

A radiation image pick-up device of the present invention, which has a wavelength converter for performing wavelength conversion on an incident radiation and a conversion substrate having conversion elements arranged in a two-dimensional array, the conversion elements converting into an electrical signal the radiation having been subjected to the wavelength conversion, the device comprising: correction image obtaining means for obtaining a plurality of correction images while changing the energy of the radiation of the incident radiation in the absence of an object, object image obtaining means for obtaining an object image in the presence of an object by emitting a radiation to the object, and correcting means for correcting the object image by using the correction image having been obtained under an energy of the radiation condition closest to an energy of the radiation of the obtained object image.

Another embodiment of the radiation image pick-up device according to the present invention, which has a wavelength converter for performing wavelength conversion on an incident radiation and a conversion substrate having conversion elements arranged in a two-dimensional array, the conversion elements converting into an electrical signal the radiation having been subjected to the wavelength conversion, the device comprising: correction image obtaining means for obtaining a plurality of correction images while changing the energy of the radiation of the incident radiation in the absence of an object, object image obtaining means for obtaining an object image in the presence of an object by emitting a radiation to the object, and correcting means for correcting the object image by using another correction image calculated newly from a first correction image having been obtained under an energy of the radiation condition closest to an energy of the radiation-of the obtained object the obtained object image and a second correction image having been obtained under the second closest energy of the radiation condition.

Still another embodiment of the radiation image pick-up device according to the present invention, which has a conversion substrate having direct radiation conversion elements arranged in a two-dimensional array, the conversion elements directly converting an incident radiation into an electrical signal, the device comprising: correction image obtaining means for obtaining a plurality of correction images while changing the energy of the radiation of the incident radiation in the absence of an object, object image obtaining means for obtaining an object image in the presence of an object by emitting a radiation to the object, and correcting means for correcting the object image by using the correction image having been obtained under an energy of the radiation condition closest to an energy of the radiation of the obtained object image.

Still another embodiment of the radiation image pick-up device according to the present invention, which has a conversion substrate having direct radiation conversion elements arranged in a two-dimensional array, the conversion elements directly converting an incident radiation into an electrical signal, the device comprising: correction image obtaining means for obtaining a plurality of correction images while changing the energy of the radiation of the incident radiation in the absence of an object, object image obtaining means for obtaining an object image in the presence of an object by emitting a radiation to the object, and correcting means for correcting the object image by using another correction image calculated newly from a first correction image having been obtained under an energy of the radiation condition closest to an energy of the radiation of the obtained object image and a second correction image having been obtained under the second closest energy of the radiation condition.

Still another embodiment of the radiation image pick-up device according to the present invention, which has a wavelength converter for performing wavelength conversion on an incident radiation and a conversion substrate having conversion elements arranged in a two-dimensional array, the conversion elements converting into an electrical signal the radiation having been subjected to the wavelength conversion, the device comprising: correction image obtaining means for obtaining a plurality of correction images while changing the energy of the radiation of the incident radiation in the presence of a reference material, object image obtaining means for obtaining an object image in the presence of an object by emitting a radiation to the object, and correcting means for correcting the object image by using the correction image having been obtained under an energy of the radiation condition closest to an energy of the radiation of the obtained object image.

Still another embodiment of the radiation image pick-up device according to the present invention, which has a wavelength converter for performing wavelength conversion on an incident radiation and a conversion substrate having conversion elements arranged in a two-dimensional array, the conversion elements converting into an electrical signal the radiation having been subjected to the wavelength conversion, the device comprising: correction image obtaining means for obtaining a plurality of correction images while changing the energy of the radiation of the incident radiation in the presence of a reference material, object image obtaining means for obtaining an object image in the presence of an object by emitting a radiation to the object, and correcting means for correcting the object image by using another correction image calculated newly from a first correction image having been obtained under an energy of the radiation condition closest to an energy of the radiation of the obtained object image and a second correction image having been obtained under the second closest energy of the radiation condition.

Still another embodiment of the radiation image pick-up device according to the present invention, which has a conversion substrate having direct radiation conversion elements arranged in a two-dimensional array, the conversion elements directly converting an incident radiation into an electrical signal, the device comprising: correction image obtaining means for obtaining a plurality of correction images while changing the energy of the radiation of the incident radiation in the presence of a reference material, object image obtaining means for obtaining an object image in the presence of an object by emitting a radiation to the object, and correcting means for correcting the object image by using the correction image having been obtained under an energy of the radiation condition closest to an energy of the radiation of the obtained object image.

Still another embodiment of the radiation image pick-up device according to the present invention, which has a conversion substrate having direct radiation conversion elements arranged in a two-dimensional array, the conversion elements directly converting into an electrical signal an incident radiation, the device comprising: correction image obtaining means for obtaining a plurality of correction images while changing the energy of the radiation of the incident radiation in the presence of a reference material, object image obtaining means for obtaining an object image in the presence of an object by emitting a radiation to the object, and correcting means for correcting the object image by using another correction image calculated newly from a first correction image having been obtained under an energy of the radiation condition closest to an energy of the radiation of the obtained object image and a second correction image having been obtained under the second closest energy of the radiation condition.

Still another embodiment of the radiation image pick-up device according to the present invention, wherein the other correction image is calculated by averaging the first correction image and the second correction image.

Still another embodiment of the radiation image pick-up device according to the present invention, wherein the wavelength converter and the conversion substrate are caused to adhere to each other by bonding.

Still another embodiment of the radiation image pick-up device according to the present invention, wherein the wavelength converter and the conversion substrate are caused to adhere to each other by vacuum evaporating the wavelength converter onto the conversion substrate.

Still another embodiment of the radiation image pick-up device according to the present invention, wherein the wavelength converter has as a matrix at least one selected from the group consisting of cesium iodide (CsI), gadolinium oxide (Gd2O3) and gadolinium oxysulfide (Gd2OS).

Still another embodiment of the radiation image pick-up device according to the present invention, wherein the conversion element consists of an amorphous silicon semiconductor material.

Still another embodiment of the radiation image pick-up device according to the present invention, wherein the direct radiation conversion element consists of a material one selected from the group consisting of amorphous selenium, gallium arsenide, mercurous iodide and lead iodide.

Still another embodiment of the radiation image pick-up device according to the present invention, wherein the reference material is a phantom containing water.

A radiation image pick-up method of the present invention for a radiation image pick-up device, which has a wavelength converter for performing wavelength conversion on an incident radiation and a conversion substrate having conversion elements arranged in a two-dimensional array, the conversion elements converting into an electrical signal the radiation having been subjected to the wavelength conversion, the method comprising: a correction image obtaining step of obtaining a plurality of correction images while changing the energy of the radiation of the incident radiation in the absence of an object, an object image obtaining step of obtaining an object image in the presence of an object by emitting a radiation to the object, and a correcting step of correcting the object image by using the correction image having been obtained under an energy of the radiation condition closest to an energy of the radiation of the obtained object image.

Another embodiment of the radiation image pick-up method according to the present invention for an image pick-up device, which has a wavelength converter for performing wavelength conversion on an incident radiation and a conversion substrate having conversion elements arranged in a two-dimensional array, the conversion elements converting into an electrical signal the radiation having been subjected to the wavelength conversion, the method comprising: a correction image obtaining step of obtaining a plurality of correction images while changing the energy of the radiation of the incident radiation in the absence of an object, an object image obtaining step of obtaining an object image in the presence of an object by emitting a radiation to the object, and a correcting step of correcting the object image by using another correction image calculated newly from a first correction image having been obtained under an energy of the radiation condition closest to an energy of the radiation of the obtained object image and a second correction image having been obtained under the second closest energy of the radiation condition.

The radiation image pick-up device of the present invention comprises the radiation image pick-up device, signal processing means for processing a signal from the radiation image pick-up device, recording means for recording a signal from the signal processing means, display means for displaying the signal from the signal processing means, transmitting means for transmitting the signal from the signal processing means, and a radiation source for generating the radiation.

According to the present invention, when a radiographed object image is corrected, white correction can be accurately performed on object images radiographed with various radiation energies (tube voltages). Thus, it is possible to reduce correction errors caused by a difference in the amount of X-ray absorption and accurately correct the object image, the difference being made by a splash, a foreign matter and so on.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

FIG. 3 is a diagram showing an X-ray absorptivity relative to a thickness of CsI;

DETAILED DESCRIPTION OF THE PREFERRED EMBODIMENTS

Embodiments of the present invention will be specifically described below in accordance with the accompanying drawings.

Embodiment 1

Embodiment 1 of the present invention will be described below in accordance with the accompanying drawings.

Figure 1:
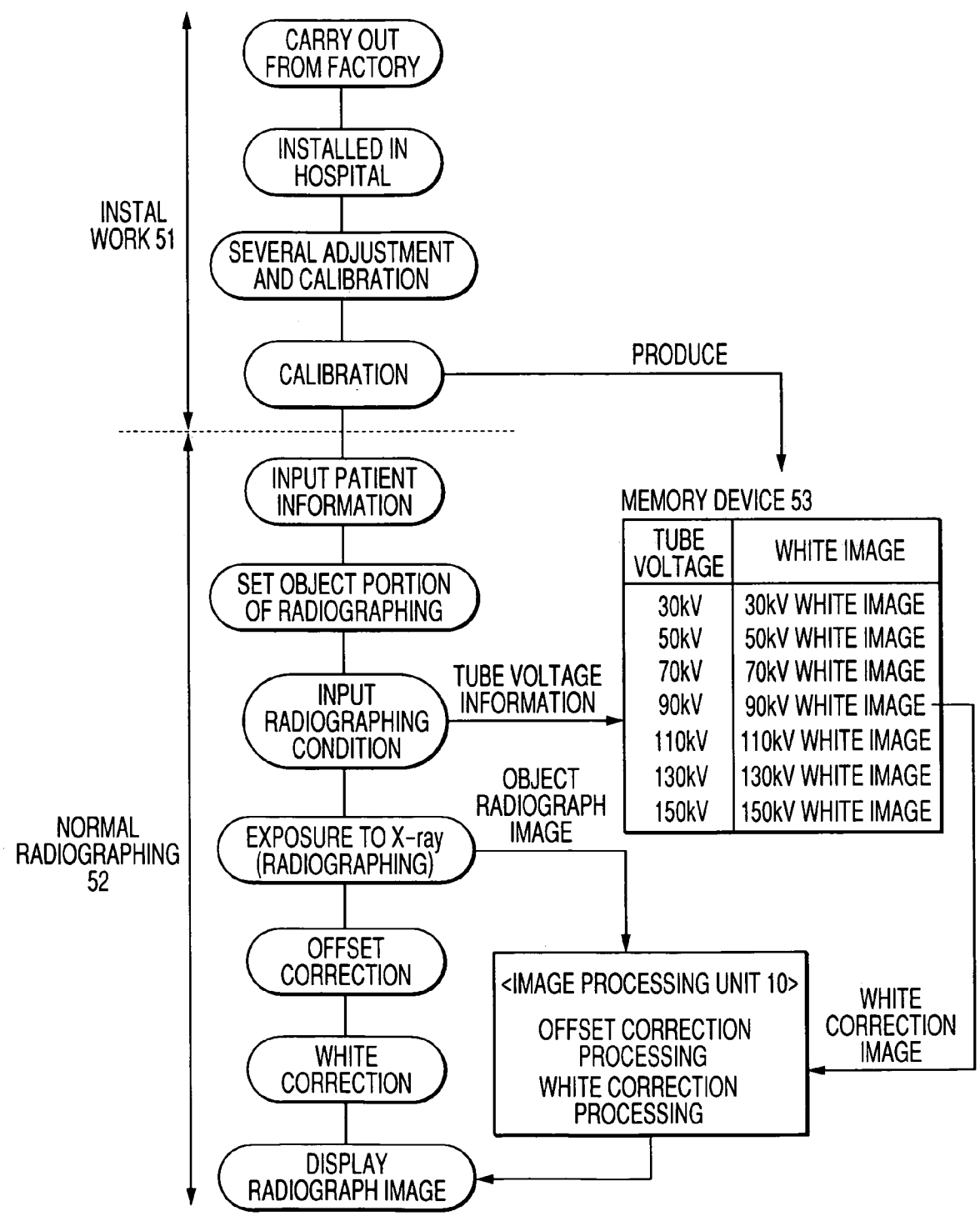
FIG. 1 is a flowchart showing an X-ray image pick-up method of Embodiment 1.

FIG. 1 is a flowchart showing an X-ray image pick-up method of Embodiment 1.

A digital X-ray image pick-up device having been carried out from a factory is installed in a hospital and subjected to several adjustments such as image formation. Thereafter, calibration is performed. The calibration is performed with no radiographed object and obtains an output of about a half of the saturation of the digital X-ray image pick-up device. Further, the calibration is performed in an area exhibiting linearity relative to a dosage (mAs value). An average value of two or more radiographed images is used to reduce quantum noise and so on. For example, an average image of ten radiographed images is used as a white image for correction.

In Embodiment 1, calibration is performed every 20 kV of tube voltage, and white images for correction are obtained at seven points of 30 kV, 50 kV, 70 kV, 90 kV, 110 kV, 130 kV and 150 kV. The seven white images obtained by calibration are stored in a reference table, which is produced in a memory device 53 and a memory for storing white images, at each of the tube voltages. In the case of the digital X-ray image pick-up device, sensor characteristics include a temperature change and a secular change and thus calibration is-performed every. week, month and year. The white images for correction are updated in each calibration.

After calibration images are obtained, an object is radiographed.

First, information on a patient, a portion to be radiographed, a radiographing mode and so on are set, and then radiographing conditions (tube voltage, mAs value and so on) are inputted. Subsequently X-rays are emitted to radiograph the object. After the radiographing, a radiographed image is transferred to an image processing unit 10 and is subjected to offset correction and white correction. During the white correction, referring to the memory device 53 and the memory for storing white correction images, a white correction image closest to the tube voltage (X-ray energy) information of the radiographing conditions is selected, the white correction image is transferred to the image processing unit 10, and white correction is performed on the radiographed image by using the white correction image.

Means for selecting a white correction image closest to the tube voltage includes a method of determining a difference between a tube voltage value of each white image stored in the memory device 53 and the memory for storing white correction images and a tube voltage of a radiographed image during the radiographing of an object, and selecting a white image having the smallest difference. In (Embodiment 1), when an object is radiographed at a tube voltage of 85 kV, a white image with a tube voltage of 90 kV is selected and transferred to the image processing unit 10, and an object image having been radiographed at 85 kV is subjected to white correction (division) using a white image with the tube voltage of 90 kV.

Figure 2:
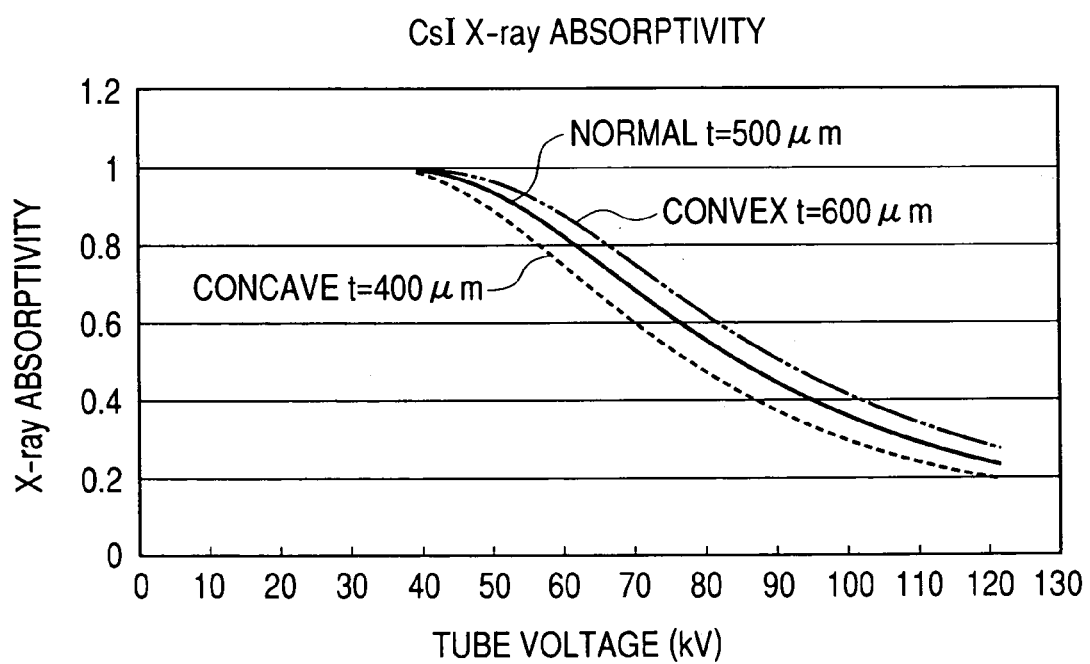
FIG. 2 is a characteristic diagram showing tube voltage—X-ray absorptivity of CsI.

In Embodiment 1, CsI:Tl having a high brightness and resolution with a thickness of 500 µm is used as a scintillator. The CsI:Tl has a splash. As described above, a splash portion has asperities. FIG. 2 is a characteristic diagram showing a tube voltage and X-ray absorptivity of CsI when a convex has a thickness of 600 µm and a concave has a thickness of 400 µm. As shown in FIG. 2, the X-ray absorbing characteristic relative to a tube voltage changes with the thickness of CsI. When the tube voltage is low, a difference in the amount of X-ray absorption is small between thicknesses. The higher tube voltage, the larger difference in the amount of absorption. Based on the amount of X-ray absorption, a comparison is made between an X-ray absorptivity ratio of the conventional art having a single white correction image (a tube voltage is 60 kV during the radiographing of the white image) and an X-ray absorptivity ratio of the present embodiment. FIG. 3 shows the results.

In the case of the conventional art having a single white correction image (a tube voltage is 60 kV during the radiographing of the white image), the X-ray absorptivity ratio of CsI is 0.56 in a normal portion, 0.52 in a splash concave, and 0.60 in a splash convex at the tube voltage of white correction radiographing and the tube voltage of object radiographing, resulting in a difference of 7 to 8% from the normal portion. In contrast, in the present embodiment, the X-ray absorptivity ratio of CsI is 1.14 in a normal portion, 1.15 in a splash concave, and 1.13 in a splash convex at the tube voltage of white correction radiographing and the tube voltage of object radiographing, so that an X-ray absorptivity ratio is reduced to 1% in the normal portion and the splash portion. In this way, a difference in the amount of X-ray absorption is reduced and thus an amount of correction error is also reduced.

Since calibration is performed every 20 kV of tube voltage in the present embodiment, the maximum difference from the radiographing tube voltage is 10 kV. By reducing the tube voltage intervals in calibration, the accuracy of white correction can be further improved.

According to the present embodiment, when a radiographed object image is corrected, a plurality of correction images are obtained beforehand while changing the radiation energy of a radiation to be incident, and the object image is corrected using a correction image obtained with a radiation energy closest to a radiation energy of the acquisition of the object image. Thus, it is possible to accurately perform white correction on object images photographed with various radiation energies (tube voltages).

Embodiment 2

Embodiment 2 of the present invention will be described below in accordance with the accompanying drawings.

Figure 4:
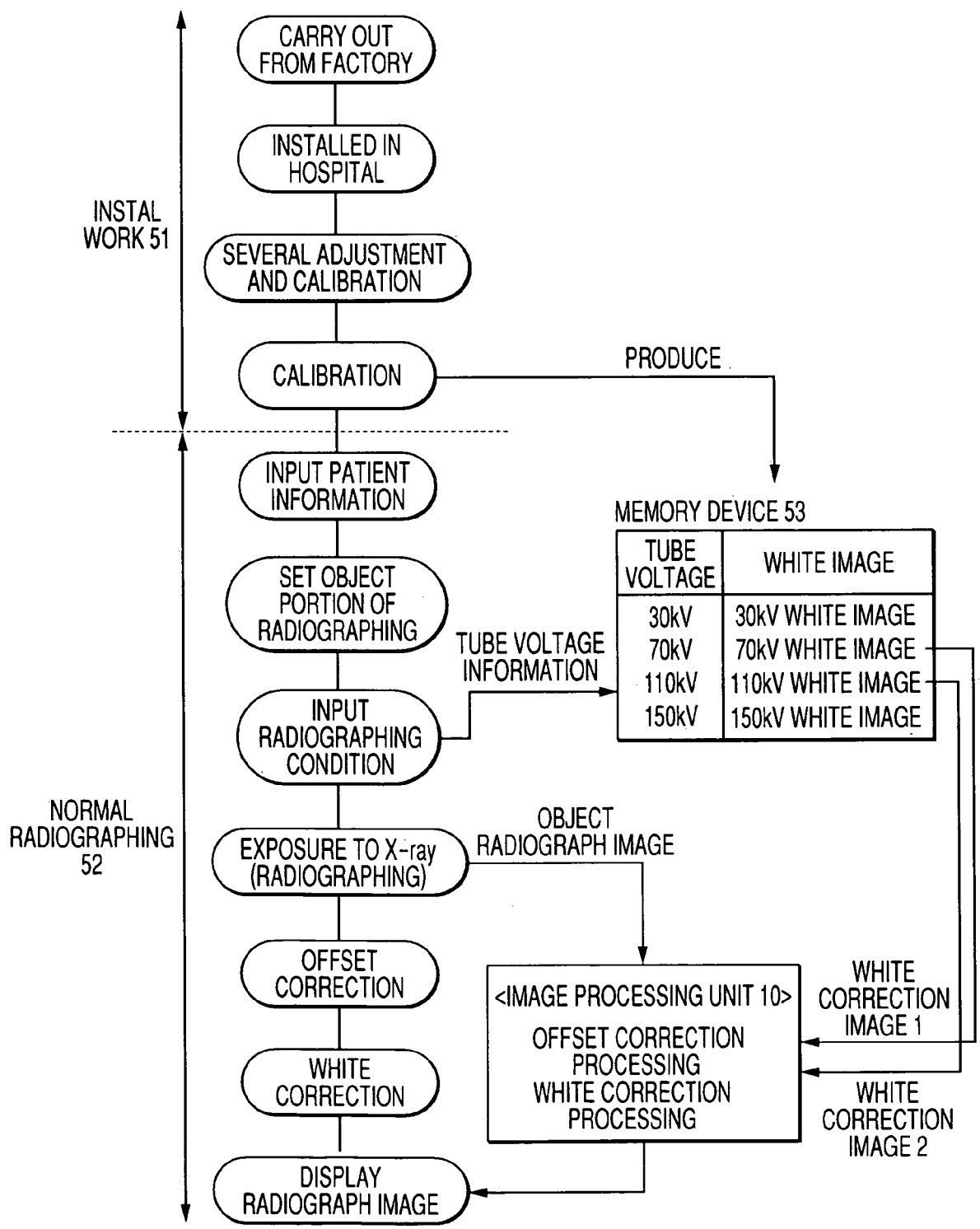
FIG. 4 is a flowchart showing an X-ray image pick-up method of Embodiment 2.

FIG. 4 is a flowchart showing an X-ray image pick-up method of Embodiment 2.

A digital X-ray image pick-up device having been carried out from a factory is installed in a hospital and subjected to several adjustments such as image formation. Thereafter, calibration is performed. The calibration is performed with no radiographed object and obtains an output of about a half of the saturation of the digital X-ray image pick-up device. Further, the calibration is performed in an area exhibiting linearity relative to a dosage (mAs value). An average value of two or more radiographed images is used to reduce quantum noise and so on. For example, an average image of ten radiographed images is used as a white image for correction.

In Embodiment 2, calibration is performed every 40 kV of tube voltage, and white images are obtained at four points of 30 kV, 70 kV, 110 kV and 150 kV. The four white images obtained by calibration are stored in a reference table, which is produced in a memory device 53 and a memory for storing white images, at each of the tube voltages. In the case of the digital X-ray image pick-up device, sensor characteristics include a temperature change and a secular change and thus calibration is performed every week, month and year. The white images are updated in each calibration.

After a calibration image is obtained, an object is radiographed.

First, information on a patient, a portion to be radiographed, a radiographing mode and so on are set, and then radiographing conditions (tube voltage, mAs value and so on) are inputted. Subsequently X-rays are emitted to radiograph the object. After the radiographing, a radiographed image is transferred to an image processing unit 10 and is subjected to offset correction and white correction. During the white correction, two white images are selected from the memory device 53 and the memory for storing white correction images. Relative to the tube voltage of the radiographing conditions, one of the two white images has a tube voltage which is higher than the radiographing tube voltage and closest to the radiographing tube voltage and the other white image has a tube voltage which is lower than the radiographing tube voltage and closest to the radiographing tube voltage.

For example, when radiographing is performed at a radiographing tube voltage of 85 kV, white images at tube voltages of 110 V and 70 kV are selected. Subsequently, the selected two white images are transferred to the image processing unit 10 and are converted to a correction image having a tube voltage of 85 kV. In this converting method, the average values of the two white images are first made equal to each other (regarding the white images at tube voltages of 70 kV and 110 kV, the output of each pixel is divided by an average value in the plane of the image). Thereafter, a weighting factor is determined according to the tube voltage 85 kV (linear approximation).

To be specific, the following equation is established:

$$85\ kV = \alpha \times 70\ kV + (1-\alpha) \times 110\ kV \rightarrow \alpha = 0.625$$

Thus, the following is obtained:

$$70\ kV\ \text{white image} \times 0.625 + 110\ kV\ \text{white image} \times 0.375 = \text{white image for } 85\ kV$$

If the above processes are performed, from a white image with a tube voltage of 70 kV and a white image with a tube voltage of 110 kV, a white image with a tube voltage of 85 kV, which is an intermediate voltage between 70 kV and 110 kV, can be produced in this processing. Although the present embodiment takes a longer time for image processing as compared with Embodiment 1, it is possible to reduce the number of times of calibration and perform image correction in a short time.

According to the present embodiment, when a radiographed object image is corrected, a plurality of correction images are obtained beforehand while changing the radiation energy of a radiation to be incident, another correction image is calculated from a correction image obtained under the closest radiation energy condition and a correction image obtained under the second closest radiation energy condition relative to a radiation energy of the acquisition of the object image, and the object image is corrected using the another correction image. Thus, it is possible to accurately perform white correction on object images photographed with various radiation energies (tube voltages).

Embodiment 3

Embodiment 3 of the present invention will be described below in accordance with the accompanying drawings.

Figure 16:
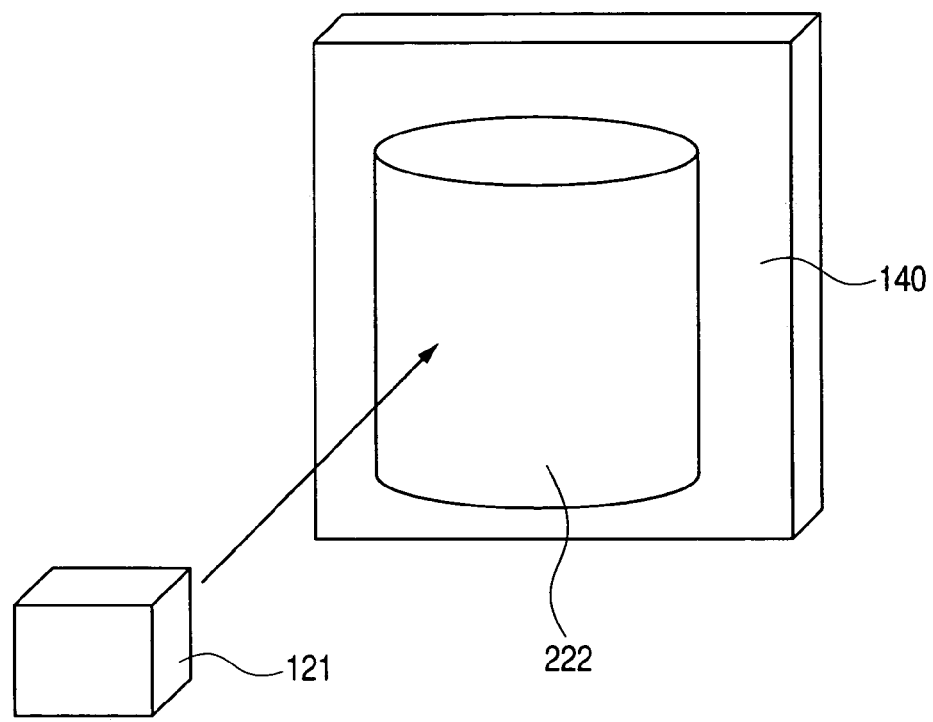
FIG. 16 is a calibration radiographing diagram of Embodiment 3.
Figure 17:
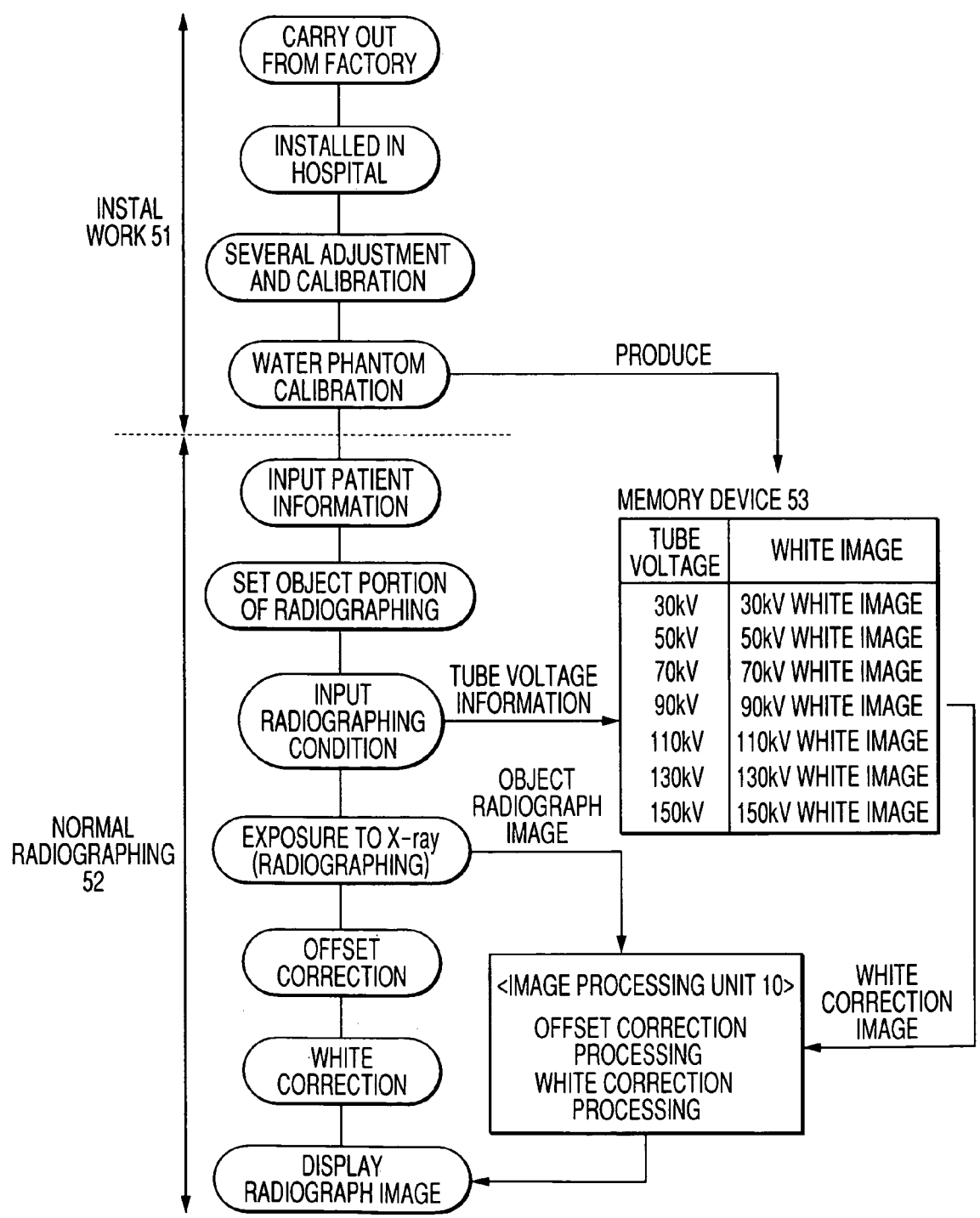
FIG. 17 is a flowchart showing an X-ray image pick-up method of Embodiment 3.

FIG. 17 is a flowchart showing an X-ray image pickup method of Embodiment 3. FIG. 16 is a calibration radiographing diagram of Embodiment 3.

Embodiment 3 of the present invention is different from Embodiment 1 only in a calibration radiographing method.

A digital X-ray image pick-up device having been carried out from a factory is installed in a hospital and subjected to several adjustments such as image formation. Thereafter, calibration is performed. In Embodiment 1, calibration is performed with no radiographed object, whereas a water phantom is used in Embodiment 3. In FIG. 16, reference numeral 121 denotes an X-ray vessel, reference numeral 140 denotes an X-ray detector, and reference numeral 222 denotes the water phantom.

Generally in calibration, radiographing is performed with no radiographed object. Since a radiation is absorbed by an object in the radiographing of the object unlike calibration radiographing, a radiation incident on the X-ray image pick-up device is changed in energy distribution. For this reason, in the present embodiment, calibration radiographing is performed using as an object a water phantom which is close to the composition of a human body (a human body has a water content of about 50 to 60%). Since an object is a human body, a water phantom is used in this embodiment of the present invention. When the object is a different material, a correction image is obtained using a reference material close to the object.

(X-ray Image Pick-up Device and X-ray Image Pick-up System)

The following will describe an X-ray image pick-up device and an X-ray image pick-up system for implementing the X-ray image pick-up method of Embodiments 1, 2 and 3.

Figure 5:
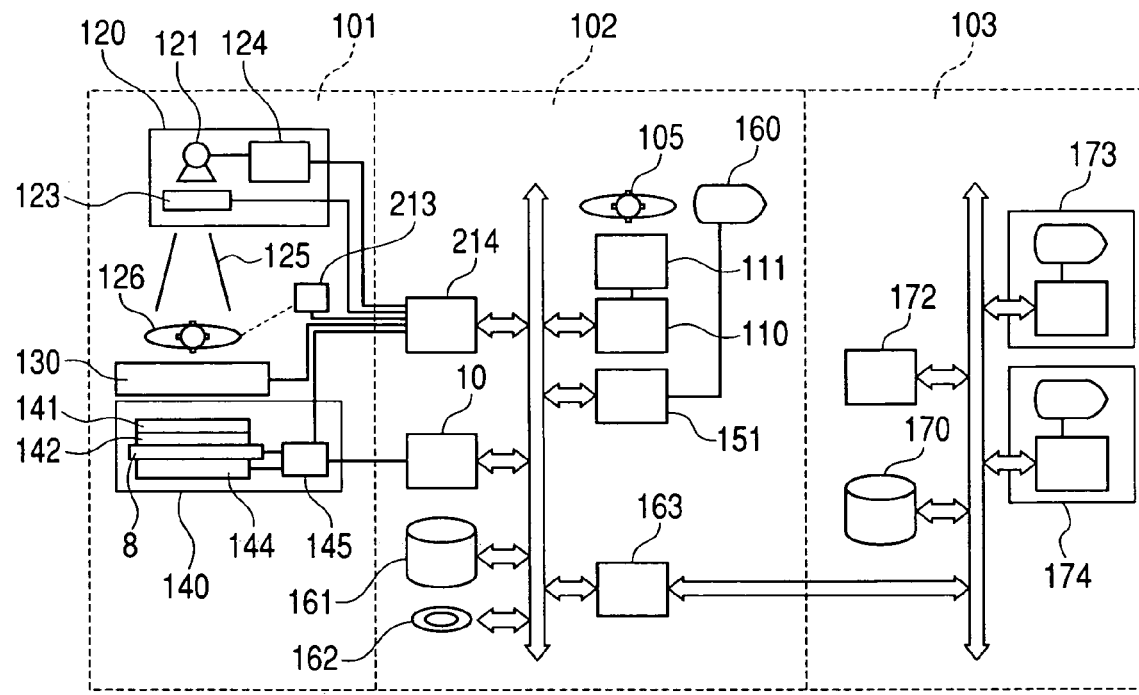
FIG. 5 is a schematic structural diagram showing an X-ray image pick-up system of the present invention.

FIG. 5 is a schematic structural diagram showing the X-ray image pickup system of the present invention.

The X-ray image pick-up system is constituted of an X-ray room 101, an X-ray control room 102 and a diagnosis room 103. The overall operations of the X-ray image pick-up system are controlled by a system control unit 110 provided in the X-ray control room 102. Further, the X-ray image pick-up device of the present invention is mainly constituted of an X-ray detector 140 (described later), an imaging control unit 214 and the image processing unit 10.

An operator interface 111 includes a touch panel on a display, a mouse, a keyboard, a joy stick and a foot switch. By using the operator interface 111, an operator 105 can make settings such as radiographing conditions (including a static image, a moving image, a tube voltage, a tube current and irradiation time), radiographing timing, image processing conditions, a subject ID and a method of processing captured images. Most information is transferred from a radiation information system (not shown) and thus individual inputs are not necessary. An important work of the operator 105 is confirmation of radiographed images. That is, the operator 105 decides whether an angle is correct or not, a patient moves or not, and image processing is proper or not.

The system control unit 110 provides the imaging control unit 214, which is responsible for an X-ray image pick-up sequence, with an instruction on the radiographing conditions based on an instruction from the operator 105 or the radiation information system, and then the system control unit 110 captures data. Then, the imaging control unit 214 drives an X-ray generator 120 serving as a radiation source, a bed 130 for radiographing and the X-ray detector 140 in response to the instruction, captures image data, and transfers the image data to the image processing unit 10. Thereafter, the imaging control unit 214 performs image processing designated by the operator 105 and provides a display on a display 160. At the same time, the image processing unit 10 stores, in an external memory device 161, raw data having been subjected to basic image processing of offset correction and white correction.

The image processing unit 10 includes a configuration for performing white correction of Embodiments 1, 2 and 3. Whenever necessary, the image processing unit 10 reads a white correction image stored at each tube voltage in the external memory device 161 and performs white correction. A memory specific for white correction images may be provided between the image processing unit 10 and the external memory device 161 to perform faster operations. In this way, the image processing unit 10 and the external memory device 161 of FIG. 5 are responsible for white correction which was discussed in Embodiments 1, 2 and 3.

Moreover, the system control unit 110 performs image processing again and displays reproduction, transfers image data to apparatuses and stores the data therein on a network, provides a display, and performs printing on a film in response to an instruction from the operator 105.

The following explanation will be made according to the flow of a signal.

The X-ray generator 120 of the X-ray room 101 includes an X-ray vessel 121, an X-ray diaphragm 123 and a high voltage source 124. The X-ray vessel 121 is driven by the high voltage source 124 controlled by the imaging control unit 214 and emits an X-ray beam 125. The X-ray diaphragm 123 is driven by the imaging control unit 214 and shapes the X-ray beam 125 so as to prevent an unnecessary X-ray irradiation caused by a change of an image pick-up area.

The X-ray beam 125 from the X-ray vessel 121 is emitted to a subject 126 lying on the bed 130 for radiographing. The bed 130 for radiographing is driven based on an instruction from the imaging control unit 214. The X-ray beam 125 having been emitted to the subject 126 passes through the subject 126 and the bed 130 for radiographing, and then the X-ray beam 125 is incident on the X-ray detector 140.

The X-ray detector 140 includes a grid 141, a fluorescent screen 142, a photodetector array 8, an X-ray exposure monitor 144 and a driving circuit 145. The grid 141 reduces the influence of X-ray scattering caused by the passage through the subject 126. The grid 141 is composed of an X-ray low absorption member and an X-ray high absorption member. For example, the grid 141 has a strip structure of Al and Pb. The grid 141 is vibrated in response to an instruction from the imaging control unit 214 during the irradiation of X-rays in order to prevent a grid ratio of the photodetector array 8 and the grid 141 from causing a moiré.

In the fluorescent screen 142, a fluorescence of a visible area is obtained by recombination energy when the matrix of the scintillator is excited by a high-energy X-ray and is recombined. The fluorescence includes a matrix such as $CaWO_4$ and $CdWO_4$ and a luminescent center such as CsI:Tl and ZnS:Ag which are activated in a parent body. The photodetector array 8 is adjacent to the fluorescent screen 142. The photodetector array 8 converts a photon into an electrical signal.

The X-ray exposure monitor 144 monitors an amount of transmitted X-rays. X-rays may be directly detected using a light-receiving element of a crystalline silicon and light may be detected from the fluorescent screen 142. In this example, a visible radiation (proportionate to an amount of X-rays) having passed through the photodetector array 8 is detected by an amorphous silicon light-receiving element which is formed as a film on the back of the photodetector array 8 and information about the detection is transmitted to the imaging control unit 214. Then, the imaging control unit 214 drives the high voltage source 124 based on the detection information and interrupts or adjusts an X-ray. The driving circuit 145 drives the photodetector array 8 under the control of the imaging control section 214 and reads signals from pixels.

An image signal from the X-ray detector 140 is transferred from the X-ray room 101 to the image processing unit 10 in the X-ray control room 102. In this transfer, since high noise occurs in the X-ray room 101 due to the generation of X-rays, image data may not be transferred accurately. Thus, a transfer passage has to have high resistance to noise. It is preferable to provide a transmission system having an error correcting function and, for example, it is preferable to use a twisted pair, which has a shielding function by means of a differential driver, and a transfer passage of an optical fiber.

The image processing unit 10 switches display data in response to an instruction from the imaging control unit 214. Additionally, the image processing unit 10 performs image data correction (offset correction, white correction), spatial filtering, recursive processing and so on in real time. The image processing unit 10 can also perform grayscale processing, scattered radiation correction, various kinds of spatial frequency processing and so on. An image processed by the image processing unit 10 is displayed on the display 160 via a display adaptor 151. Further, a basic image having been subjected only to data correction is stored in the external memory device 161 concurrently with the real-time image processing. A fast data storage device of a large capacity and high reliability desirably serves advantageously as the high-speed memory device 161. For example, a hard disc array such as RAID is desirable.

The image data having been stored in the external memory device 161 in response to an instruction from the operator 105 is stored in an external memory device 162. At this point, the image data is so reconfigured as to satisfy predetermined specifications (e.g., IS&C), and then the image data is stored in the external memory device. For example, the external memory device includes a magneto-optical disc 162 and a hard disc in a file server 170 on a LAN.

The X-ray image pick-up device can be connected to the LAN via a LAN board 163 and has data compatibility with HIS. Naturally the LAN connects a plurality of X-ray image pick-up devices. The LAN also connects a monitor 174 for displaying moving and static images, a file server 170 for filing image data, an image printer 172 for outputted an image to a film and an image processing terminal 173 for performing complicated image processing and diagnosis support. The X-ray image pick-up device outputs image data according to a predetermined protocol (e.g., DICOM). Besides, a doctor can perform telediagnosis in real time during X-ray imaging via a monitor connected to the LAN.

Figure 6:
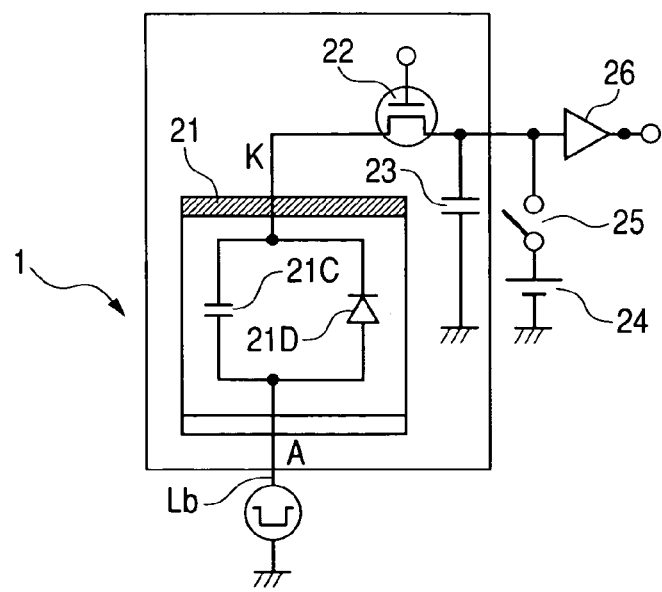
FIG. 6 is a diagram showing an example of an equivalent circuit in a photodetector array.

FIG. 6 is a diagram showing an example of an equivalent circuit in the photodetector array 8.

Hereinafter, two-dimensional amorphous silicon photoelectric conversion elements will be described below as the photodetector array 8. A sensing element is not particularly limited. For example, also in the case of another solid-state imaging device (such as a charge coupled device) or a device such as a photomultiplier, an AD converter has the same function and configuration.

A device in the photodetector array 8 is constituted of a photoelectric conversion element 21 and a switching TFT 22 for controlling the accumulation and reading of charge. In general, the device is formed by amorphous silicon (α-Si) provided on a glass substrate. The photoelectric conversion element 21 comprises a capacitor 21-C and a photodiode 21-D. In this example, the capacitor 21-C may be a parasitic capacitor or a capacitor added to improve the dynamic range of the photodiode 21-D. The anode A of the diode 21-D is connected to a bias wire Lb, which is a common electrode, and a cathode K of the diode-21-D is connected to a switching TFT 22, which can be freely controlled to read charge accumulated in the capacitor 21-C. In this example, the switching TFT 22 is a thin-film transistor connected between the cathode K of the diode 21-D and an amplifier 26 for reading charge.

The switching TFT 22 operates a switching element 25 for resetting by means of signal charge and resets the capacitor 21-C. Thereafter, a radiation 1 is emitted to the photoelectric conversion element 21. Charge is generated according to a radiation dosage from the photodiode 21-D and is stored in the capacitor 21-C. Then, the switching TFT 22 operates again the switching element 25 for resetting and transfers charge accumulated in the capacitor 21-C to a capacitive element 23. Then, an amount of charge generated by the photodiode 21-D is read by a preamplifier 26 as a potential signal, and then an incident radiation dosage is detected by AD conversion.

Figure 7:
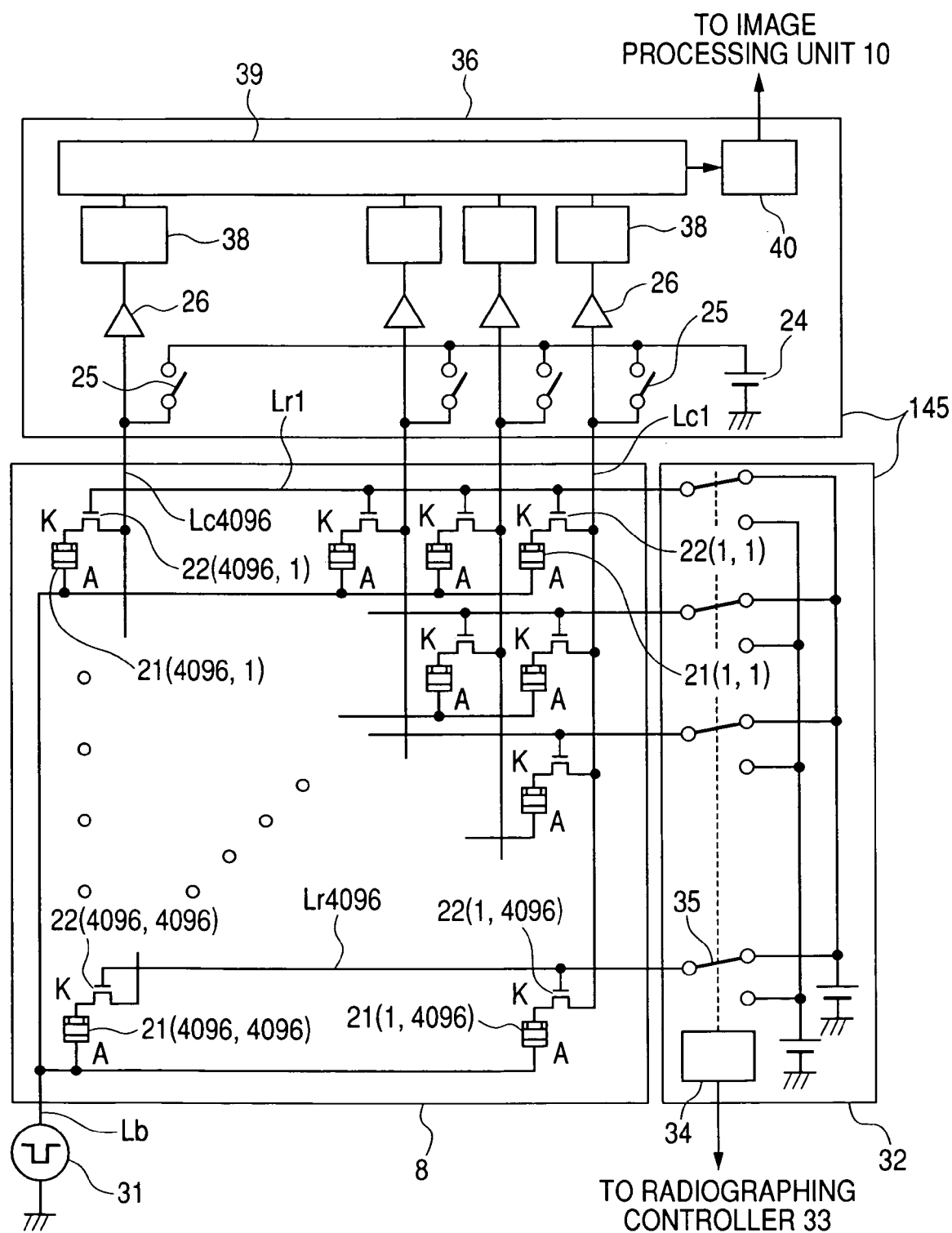
FIG. 7 is an equivalent circuit diagram showing a photoelectric converter arranged in a two-dimensional manner.
Figure 8:
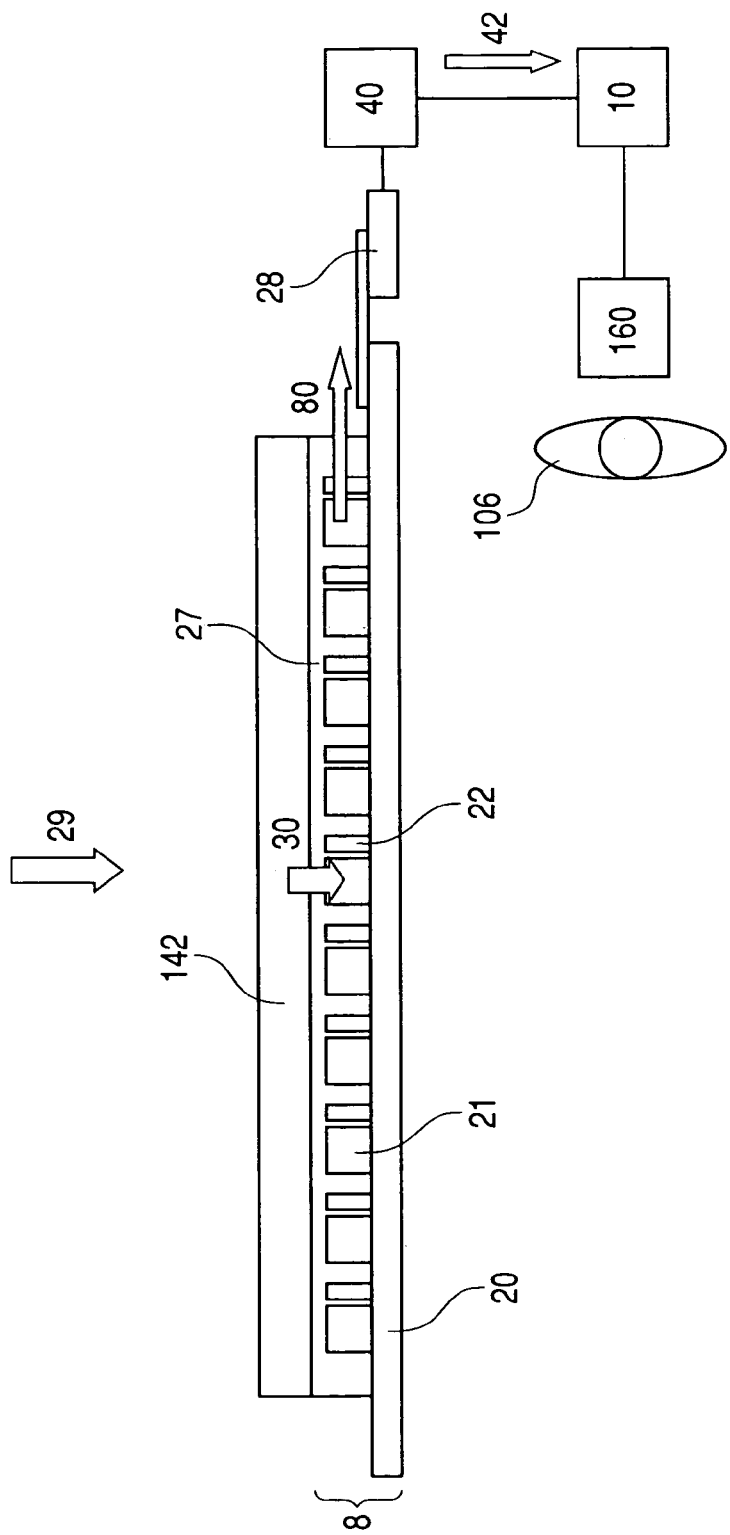
FIG. 8 is a schematic sectional view showing a digital X-ray image pick-up device of the conventional art.
Figure 9:
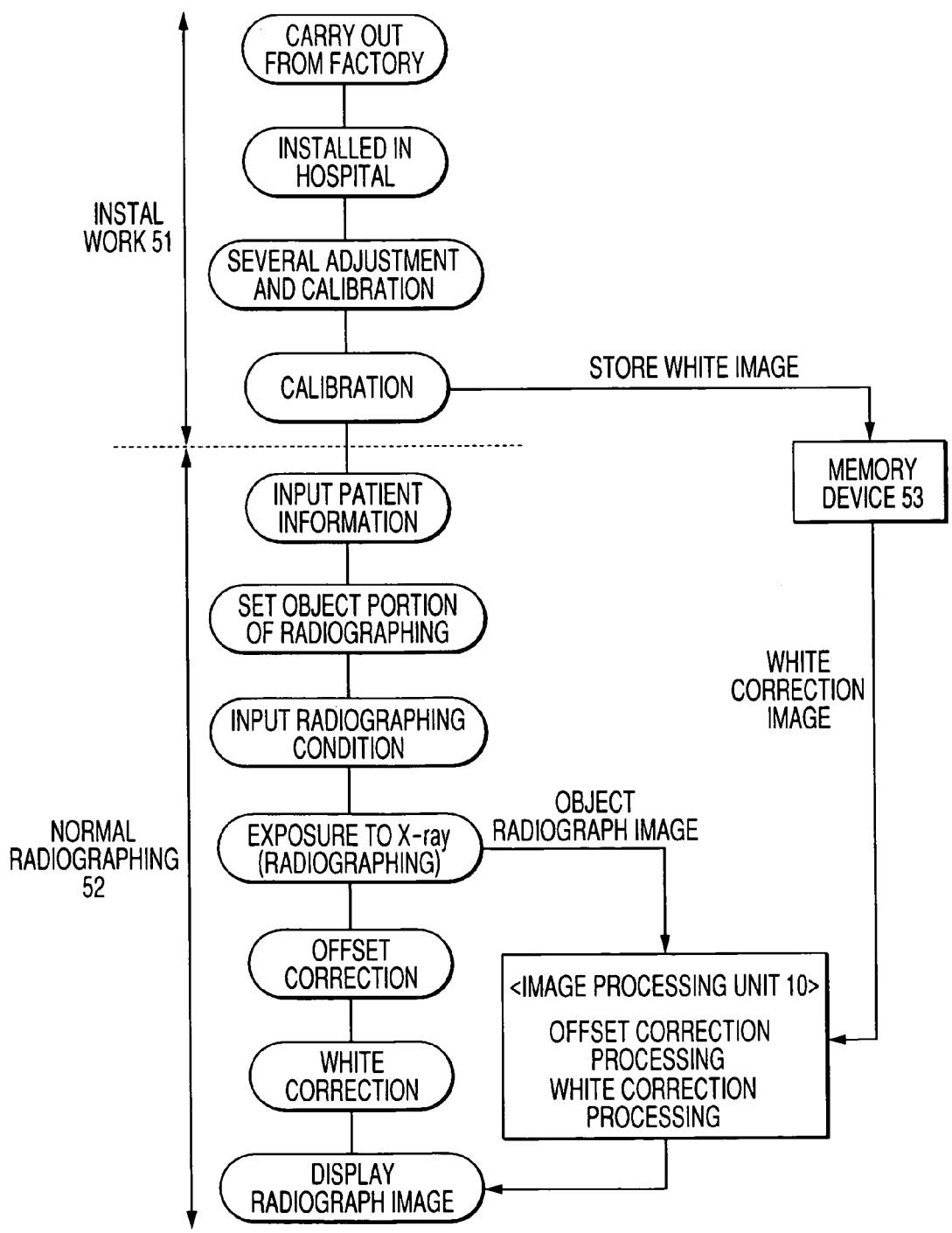
FIG. 9 is a flowchart showing a digital X-ray image pick-up method of the conventional art.
Figure 10:
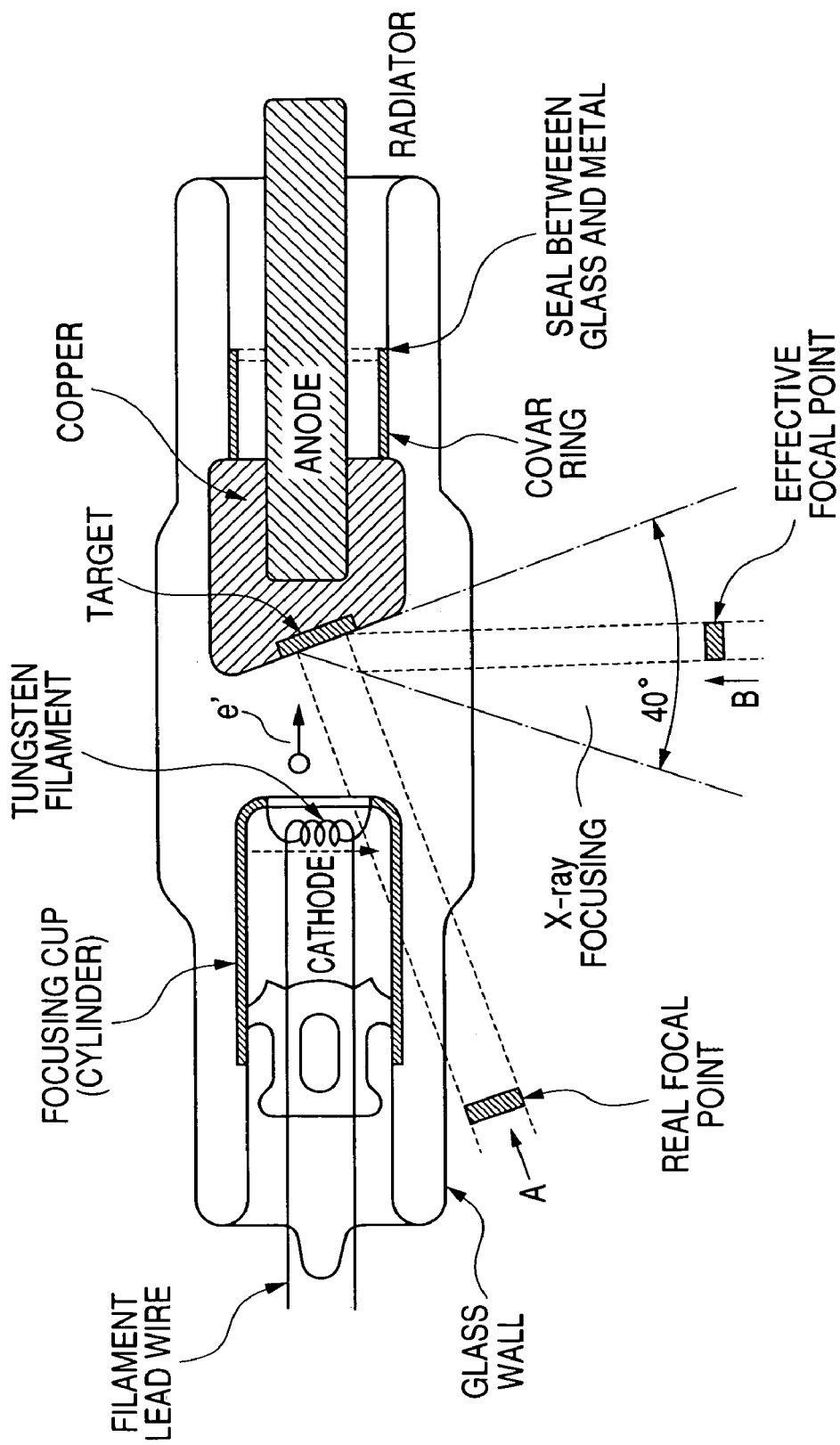
FIG. 10 is a schematic sectional view showing an X-ray tube serving as an X-ray source in an X-ray generator.
Figure 11:
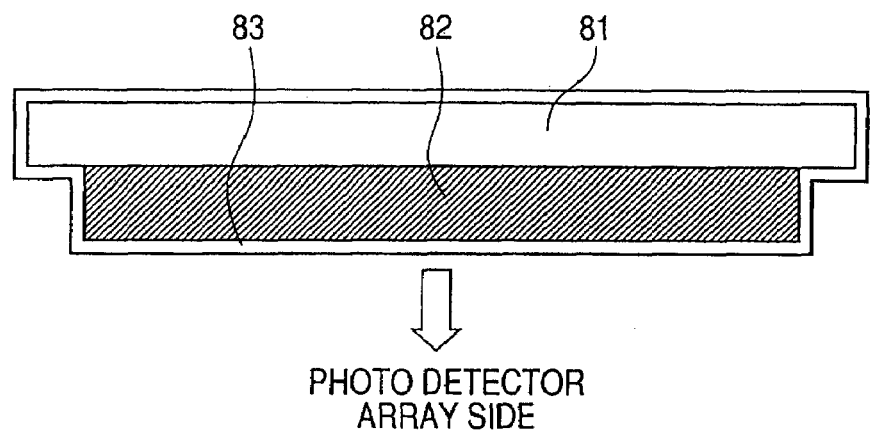
FIG. 11 is a schematic sectional view showing a CsI fluorescent screen.
Figure 12:
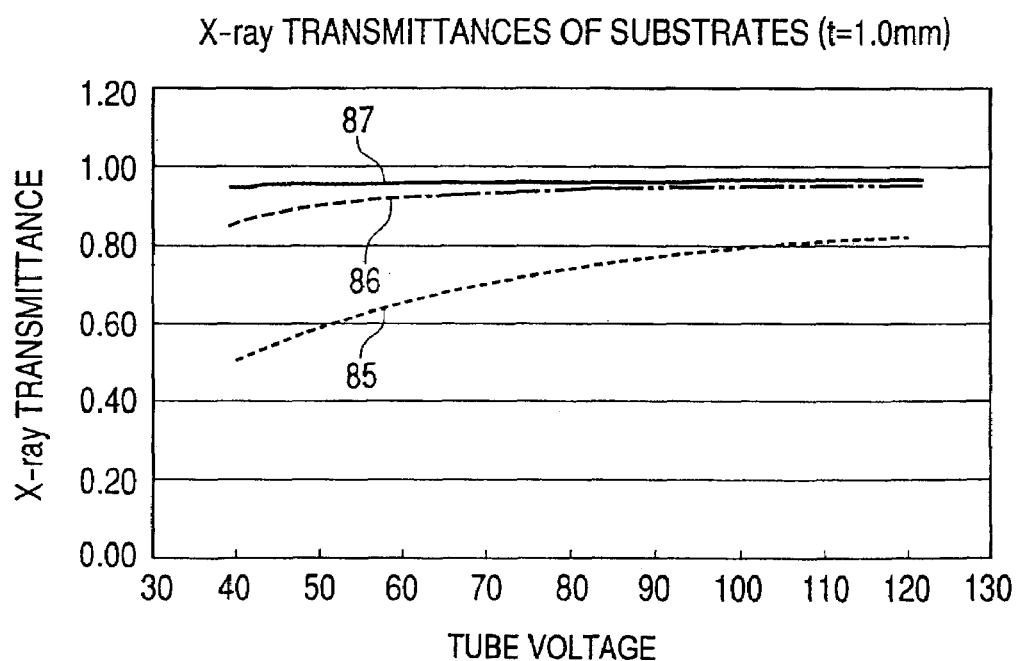
FIG. 12 is a characteristic diagram showing tube voltage—X-ray transmittance of glass, aluminum and amorphous carbon which are mainly used as substrates.
Figure 13:
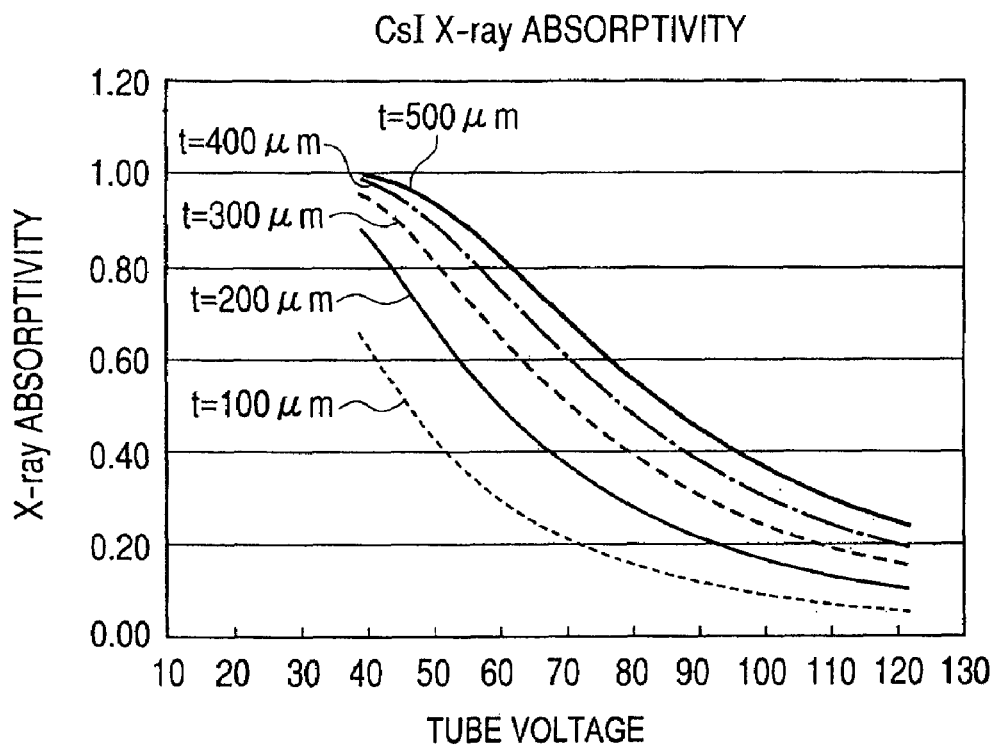
FIG. 13 is a characteristic diagram showing X-ray absorptivities in CsI which is 100 to 500 µm in thickness.
Figure 14:
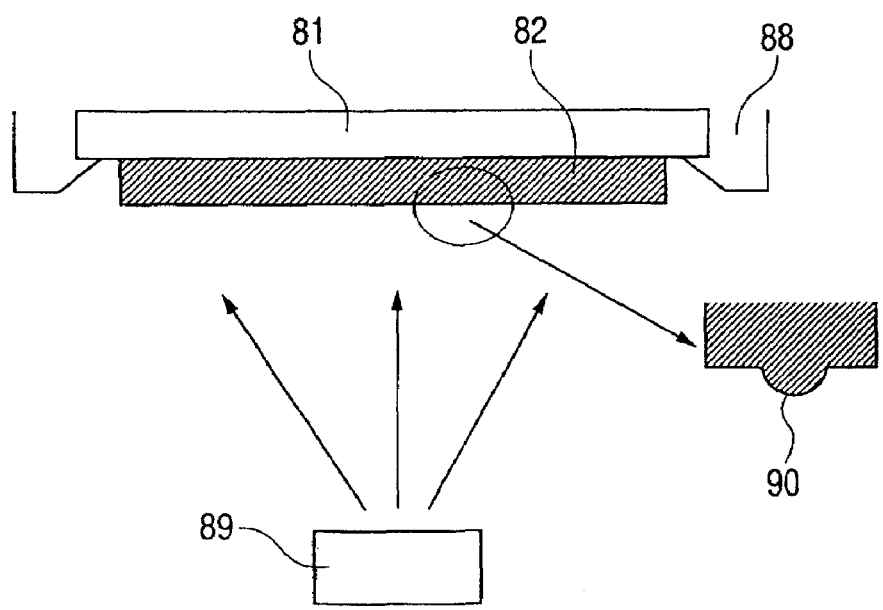
FIG. 14 is a schematic diagram showing that a substrate of CsI is formed by vacuum deposition.
Figure 15A:
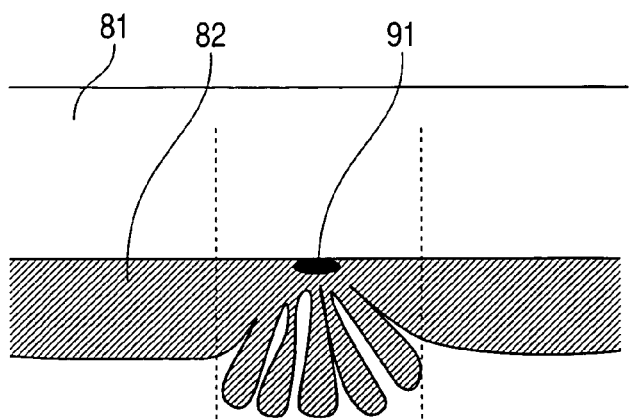
FIGS. 15A, 15B, 15C and 15D are diagrams showing abnormal growth of CsI used as a scintillator (wavelength converter)
Figure 15B:
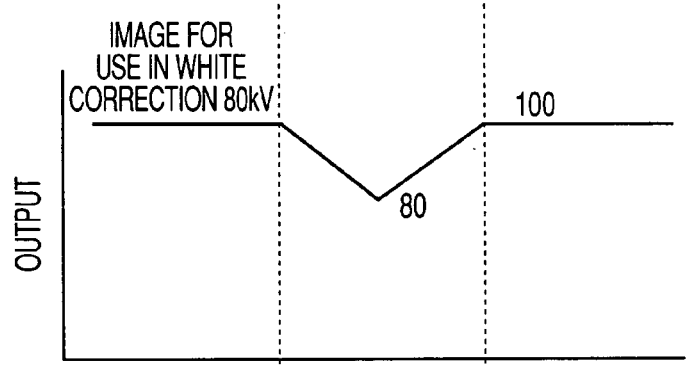
Figure 15C:
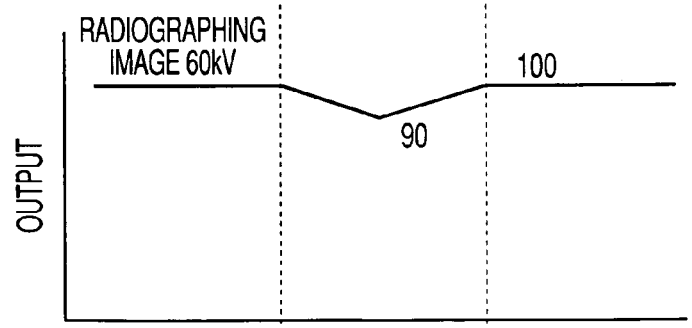
Figure 15D:
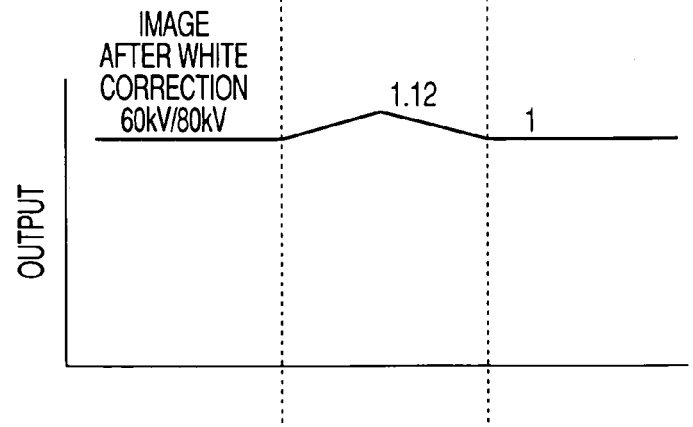

FIG. 7 is an equivalent circuit diagram showing a photoelectric converter (corresponding to the photodetector array 8 and the driving circuit 145 in FIG. 5) arranged in a two-dimensional manner. The following will specifically describe photoelectric conversion when the photoelectric conversion element of FIG. 6 is extendedly arranged in a two-dimensional manner.

The photodetector array 8 is constituted of about 2000× 2000 to 4000×4000 pixels and has an array area of about 200×200 mm to 500×500 mm. The photodetector array 8 shown in FIG. 7 is constituted of 4096×4096 pixels and has an array area of 430×430 mm. Thus, one pixel is about 105 μm×105 μm in size. One block has 4096 pixels wired in a lateral direction and 4096 lines are sequentially arranged in a longitudinal direction, so that the pixels are arranged in a two dimensional manner.

In the above-described example, the photodetector array 8 of 4096×4096 pixels is constituted of a single substrate. The photodetector array 8 of 4096×4096 pixels may be constituted of four photodetectors each of which has 2048× 2048 pixels. When one photodetector array 8 is constituted of four photodetectors each of which has 2048 ×2048 pixels, yields are increased by divided manufacturing.

As described above, one pixel is constituted of the photoelectric conversion element 21 and the switching TFT 22. 21—(1, 1) to 21—(4096, 4096) in FIG. 7 correspond to the photoelectric conversion elements 21 described above. Reference character K denotes the cathode of the photodetector diode and reference character A denotes the anode of the photodetector diode. Further, 22—(1, 1) to 22—(4096, 4096) correspond to the switching TFTs 22 described above.

Electrodes K of photoelectric conversion elements 21— (m, n) in each column of the two-dimensional photodetector array 8 are connected to a common column signal line (Lc1 to 4096) of each column via the source and drain conducting paths of the corresponding switching TFTs 22—(m, n). For example, the photoelectric conversion elements 21—(1, 1) to (1, 4096) in a column 1 are connected to a first column signal wire Lc1. Further, electrodes A of the photoelectric conversion elements 21 in each row are connected to a bias power supply 31, which operates the mode described above, in common via a bias wire Lb.

The gate electrodes of the TFTs 22 in each row are connected to a row selection wire (Lr1 to 4096). For example, the TFTs 22—(1, 1) to (4096, 1) in a row 1 are connected to the row selecting wire Lr1. The row selecting wire Lr is connected to an imaging control unit 33 via a line selector 32.

For example, the line selector 32 is constituted of an address decoder 34 and 4096 switching elements 35. With this configuration, a given line Lrn can be read. In the case of the simplest configuration, the line selector 32 can be constituted only of a shift register which is used in a liquid crystal display and so on.

The column signal wire Lc is connected to a signal reader 36 which is controlled by the imaging control unit 33. The signal reader 36 is constituted of a reset reference power supply 24, a resetting switch 25 for resetting the column signal wire Lr at the reference potential of the reset reference power supply 24, the preamplifier 26 for amplifying a signal potential, a sample/hold circuit 38, an analog multiplexer 39 and an AD converter 40. A signal from each of the column signal wires Lcn is amplified by the preamplifier 26 and is held by the sample/hold circuit 38. Further, the output is sequentially outputted to the AD converter 40 via the analog multiplexer 39, is converted into a digital value, and is transferred to the image processing unit 10.

In the photoelectric converter, 4096×4096 pixels are divided by the 4096 lines Lcn, the outputs of 4096 pixels in each row are outputted at the same time, and the outputs are sequentially outputted by the analog multiplexer 39 to the AD converter 40 through the column signal lines Lc, the preamplifiers 26-1 to 4096 and the sample/hold circuits 38-1 to 4096. In FIG. 7, although it appears that the AD converter 40 is constituted of one element, AD conversion is simultaneously performed by 4 to 32 systems in reality. This is because it is necessary to reduce a reading time of an image signal without unnecessarily increasing an AD conversion rate of an analog signal band.

An accumulation time and an AD conversion time have a close relationship. High-speed AD conversion increases the band of the analog circuit, resulting in difficulty in obtaining a desired S/N. Therefore, it is necessary to reduce a reading time of an image signal without unnecessarily increasing an AD conversion speed. AD conversion is performed for this purpose by using a number of AD converters 40. In this case, the cost increases. Hence, it is necessary to select a proper value in consideration of this point.

Since the irradiation time of radiations is about 10 to 500 msec, it is proper to set a capturing time or a charge accumulation time of a full screen on the order of 100 msec or shorter. For example, when the analog signal band is set at about 50 MHz and AD conversion is performed at a sampling rate of, e.g., 10 MHz in order to sequentially drive all the pixels and capture an image in 100 msec, the AD converters 40 of at least four systems are necessary. In this image pick-up device, AD conversion is performed simultaneously by 16 systems. Outputs from the AD converters 40 of 16 systems are inputted to the corresponding memories (FIFO, etc., not shown) of 16 systems. By selecting and switching the memories, image data corresponding to a scanning line of one continuous line is transferred to the subsequent image processing unit 10 or the memories. Thereafter, the data is displayed as an image or a graph on a display device such as a display.

In the embodiments of the present invention, the X-ray image pick-up device having the fluorescent screen 142 was described as an example. The present invention is not limited to this example and is applicable to an X-ray image pick-up device having a conversion substrate where direct X-ray conversion elements for directly converting incident X-rays into electrical signals are arranged in a two-dimensional array. In this case, the material of the direct X-ray conversion element is preferably selected from the group consisting of amorphous selenium, gallium arsenide, mercurous iodide and lead iodide.

According to the radiation image pick-up device of the present embodiment, when a radiographed image is corrected, white correction can be accurately performed on object images having been radiographed with various radiation energies (tube voltages).

As many apparently widely different embodiments of the present invention can be made without departing from the spirit and scope thereof, it is to be understood that the invention is not limited to the specific embodiments thereof except as defined in the claims.

This application claims priority from Japanese Patent Application Nos. 2003-391063 filed on Nov. 20, 2003 and 2004-174520 filed on Jun. 11, 2004, which are hereby incorporated by reference herein.

What is claimed is:

1. A radiation image pick-up device, which has a wavelength converter for performing wavelength conversion on an incident radiation and a conversion substrate having conversion elements arranged in a two-dimensional array, the conversion elements converting into an electrical signal the radiation having been subjected to the wavelength conversion, the device, comprising:

correction image obtaining means for obtaining a plurality of correction images while changing an energy of the radiation of the incident radiation in an absence of an object;

object image obtaining means for obtaining an object image in a presence of an object by emitting a radiation to the object; and correcting means for correcting the object image by using the correction image having been obtained under an energy of the radiation condition closest to an energy of the radiation of the obtained object image.

2. The radiation image pick-up device according to claim 1, wherein the wavelength converter and the conversion substrate are caused to adhere to each other by bonding.

3. The radiation image pick-up device according to claim 1, wherein the wavelength converter and the conversion substrate are caused to adhere to each other by vacuum evaporating the wavelength converter onto the conversion substrate.

4. The radiation image pick-up device according to claim 1, wherein the wavelength converter has as a matrix at least one selected from the group consisting of cesium iodide, gadolinium oxide and gadolinium oxysulfide.

5. The radiation image pick-up device according to claim 1, wherein the conversion element consists of an amorphous silicon semiconductor material.

6. A radiation image pick-up device, which has a wavelength converter for performing wavelength conversion on an incident radiation and a conversion substrate having conversion elements arranged in a two-dimensional array, the conversion elements converting into an electrical signal the radiation having been subjected to the wavelength conversion, the device comprising:

correction image obtaining means for obtaining a plurality of correction images while changing an energy of the radiation of the incident radiation in an absence of an object;

object image obtaining means for obtaining an object image in a presence of an object by emitting a radiation to the object; and correcting means for correcting the object image by using another correction image calculated newly from a first correction image having been obtained under an energy of the radiation condition closest to an energy of the radiation of the obtained object image and a second correction image having been obtained under a second closest energy of the radiation condition.

7. The radiation image pick-up device according to claim 6, wherein the other correction image is calculated by averaging the first correction image and the second correction image.

8. A radiation image pick-up method for a radiation image pick-up device, which has a wavelength converter for performing wavelength conversion on an incident radiation and a conversion substrate having conversion elements arranged in a two-dimensional array, the conversion elements converting into an electrical signal the radiation having been subjected to the wavelength conversion, the method, comprising:
a correction image obtaining step of obtaining a plurality of correction images while changing an energy of the radiation of the incident radiation in an absence of an object;
an object image obtaining step of obtaining an object image in a presence of an object by emitting a radiation to the object; and
a correcting step of correcting the object image by using the correction image having been obtained under an energy of the radiation condition closest to an energy of the radiation of the obtained object image.

9. A radiation image pick-up method for an image pick-up device, which has a wavelength converter for performing wavelength conversion on an incident radiation and a conversion substrate having conversion elements arranged in a two-dimensional array, the conversion elements converting into an electrical signal the radiation having been subjected to the wavelength conversion, the method, comprising:
a correction image obtaining step of obtaining a plurality of correction images while changing an energy of the radiation of the incident radiation in an absence of an objecy;
an object image obtaining step of obtaining an object image in a presence of an object by emitting a radiation to the object; and
a correcting step of correcting the object image by using another correction image calculated newly from a first correction image having been obtained under an energy of the radiation condition closest to an energy of the radiation of the obtained object image and a second correction image having been obtained under a second closest energy of the radiation condition.

10. A radiation image pick-up device, which has a conversion substrate having direct radiation conversion elements arranged in a two-dimensional array, the conversion elements directly converting an incident radiation into an electrical signal, the device, comprising:
correction image obtaining means for obtaining a plurality of correction images while changing an energy of the radiation of the incident radiation in an absence of an object;
object image obtaining means for obtaining an object image in a presence of an object by emitting a radiation to the object; and
correcting means for correcting the object image by using the correction image having been obtained under an energy of the radiation condition closest to energy of the radiation of the obtained object image.

11. The radiation image pick-up device according to claim 10, wherein the direct radiation conversion element consists of a material one selected from the group consisting of amorphous selenium, gallium arsenide, mercurous iodide and lead iodide.

12. A radiation image pick-up device, which has a conversion substrate having direct radiation conversion elements arranged in a two-dimensional array, the conversion elements directly converting an incident radiation into an electrical signal, the device, comprising:
correction image obtaining means for obtaining a plurality of correction images while changing an energy of the radiation of the incident radiation in an absence of an object;
object image obtaining means for obtaining an object image in a presence of an object by emitting a radiation to the object; and
correcting means for correcting the object image by using another correction image calculated newly from a first correction image having been obtained under an energy of the radiation condition closest to an energy of the radiation of the obtained object image and a second correction image having been obtained under a second closest energy of the radiation condition.

13. The radiation image pick-up device according to claim 12, wherein the other correction image is calculated by averaging the first correction image and the second correction image.

14. A radiation image pick-up device, which has a wavelength converter for performing wavelength conversion on an incident radiation and a conversion substrate having conversion elements arranged in a two-dimensional array, the conversion elements converting into an electrical signal the radiation having been subjected to the wavelength conversion, the device, comprising:
correction image obtaining means for obtaining a plurality of correction images while changing an energy of the radiation of the incident radiation in a presence of a reference material;
object image obtaining means for obtaining an object image in a presence of an object by emitting a radiation to the object; and
correcting means for correcting the object image by using the correction image having been obtained under an energy of the radiation condition closest to an energy of the radiation of the obtained object image.

15. The radiation image pick-up device according to claim 14, wherein the reference material is a phantom containing water.

16. The radiation image pick-up device according to claim 14, wherein the wavelength converter and the conversion substrate are caused to adhere to each other by bonding.

17. The radiation image pick-up device according to claim 14, wherein the wavelength converter and the conversion substrate are caused to adhere to each other by vacuum evaporating the wavelength converter onto the conversion substrate.

18. The radiation image pick-up device according to claim 14, wherein the wavelength converter has as a matrix at least one selected from the group consisting of cesium iodide, gadolinium oxide and gadolinium oxysulfide.

19. The radiation image pick-up device according to claim 14, wherein the conversion element consists of an amorphous silicon semiconductor material.

20. A radiation image pick-up device, which has a wavelength converter for performing wavelength conversion on an incident radiation and a conversion substrate having conversion elements arranged in a two-dimensional array, the conversion elements converting into an electrical signal the radiation having been subjected to the wavelength conversion, the device, comprising:

correction image obtaining means for obtaining a plurality of correction images while changing an energy of the radiation of the incident radiation in a presence of a reference material;

object image obtaining means for obtaining an object image in a presence of an object by emitting a radiation to the object; and correcting means for correcting the object image by using another correction image calculated newly from a first correction image having been obtained under an energy of the radiation condition closest to an energy of the radiation of the obtained object image and a second correction image having been obtained under a second closest energy of the radiation condition.

21. The radiation image pick-up device according to claim 20, wherein the other correction image is calculated by averaging the first correction image and the second correction image.

22. A radiation image pick-up device, which has a conversion substrate having direct radiation conversion elements arranged in a two-dimensional array, the conversion elements directly converting an incident radiation into an electrical signal, the device, comprising:

correction image obtaining means for obtaining a plurality of correction images while changing an energy of the radiation of the incident radiation in a presence of a reference material;

object image obtaining means for obtaining an object image in a presence of an object by emitting a radiation to the object; and correcting means for correcting the object image by using the correction image having been obtained under an energy of the radiation condition closest to an energy of the radiation of the obtained object image.

23. The radiation image pick-up device according to claim 22, wherein the reference material is a phantom containing water.

24. The radiation image pick-up device according to claim 22, wherein the direct radiation conversion element consists of a material one selected from the group consisting of amorphous selenium, gallium arsenide, mercurous iodide and lead iodide.

25. A radiation image pick-up device, which has a conversion substrate having direct radiation conversion elements arranged in a two-dimensional array, the conversion elements directly converting an incident radiation into an electrical signal, the device, comprising:

correction image obtaining means for obtaining a plurality of correction images while changing an energy of the radiation of the incident radiation in a presence of a reference material;

object image obtaining means for obtaining an object image in a presence of an object by emitting a radiation to the object; and correcting means for correcting the object image by using another correction image calculated newly from a first correction image having been obtained under an energy of the radiation condition closest to an energy of the radiation of the obtained object image and a second correction image having been obtained under a second closest energy of the radiation condition.

26. The radiation image pick-up device according to claim 25, wherein the other correction image is calculated by averaging the first correction image and the second correction image.

27. A radiation image pick-up system, comprising:

the radiation image pick-up device according to any one of claims 1 to 10;

signal processing means for processing a signal from the radiation image pick-up device;

recording means for recording a signal from the signal processing means;

display means for displaying the signal from the signal processing means;

transmitting means for transmitting the signal from the signal processing means; and a radiation source for generating the radiation.

* * * * *

UNITED STATES PATENT AND TRADEMARK OFFICE
CERTIFICATE OF CORRECTION

| | | |
|---|---|---|
| PATENT NO. | : 7,342,221 B2 | |
| APPLICATION NO. | : 10/991436 | |
| DATED | : March 11, 2008 | |
| INVENTOR(S) | : Katsuro Takenaka et al. | |

It is certified that error appears in the above-identified patent and that said Letters Patent is hereby corrected as shown below:

ON TITLE PAGE [54] TITLE:

Title, "RADIATION IMAGE PICK-UP DEVICE, RADIATION IMAGE PICK-UP METHOD, AND IMAGE PICKUP SYSTEM" should read --RADIATION IMAGE PICK-UP DEVICE, RADIATION IMAGE PICK-UP METHOD, AND RADIATION IMAGE PICK-UP SYSTEM--.

COLUMN 1:

Line 3, "IMAGE" should read --RADIATION IMAGE--.

COLUMN 6:

Line 17, "radiation -of" should read --radiation of--.

COLUMN 8:

Line 7, "(Gd 2O3)" should read --$Gd_2O_3$--; and "(Gd2OS)" should read --$Gd_2OS$--.

COLUMN 10:

Line 24, "is-performed every." should read --is performed every--.

COLUMN 15:

Line 41, "outputted" should read --outputting--.

COLUMN 18:

Line 23, "device," should read --device--.

UNITED STATES PATENT AND TRADEMARK OFFICE
CERTIFICATE OF CORRECTION

PATENT NO. : 7,342,221 B2
APPLICATION NO. : 10/991436
DATED : March 11, 2008
INVENTOR(S) : Katsuro Takenaka et al.

It is certified that error appears in the above-identified patent and that said Letters Patent is hereby corrected as shown below:

COLUMN 19:

Line 16, "method," should read --method--; and
    Line 39, "objecy;" should read --object;--.

COLUMN 20:

Line 3, "one" should be deleted;
    Line 11, "device," should read --device--; and
    Line 37, "device," should read --device--.

COLUMN 21:

Line 8, "device," should read --device--.

COLUMN 22:

Line 3, "one" should be deleted; and
    Line 11, "device," should read --device--.

Signed and Sealed this

Thirtieth Day of December, 2008

JON W. DUDAS
*Director of the United States Patent and Trademark Office*